(12) United States Patent
Balaban et al.

(10) Patent No.: US 7,330,748 B2
(45) Date of Patent: Feb. 12, 2008

(54) METHOD FOR DETERMINING IN VIVO CONCENTRATION OF A METABOLITE

(75) Inventors: Robert S. Balaban, Bethesda, MD (US); Kathleen M. Ward, Arlington, VA (US); Anthony H. Aletras, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 510 days.

(21) Appl. No.: 10/948,942

(22) Filed: Sep. 24, 2004

(65) Prior Publication Data
US 2005/0059881 A1      Mar. 17, 2005

Related U.S. Application Data

(62) Division of application No. 09/959,138, filed as application No. PCT/US00/10878 on Apr. 20, 2000, now Pat. No. 6,963,769.

(60) Provisional application No. 60/130,532, filed on Apr. 21, 1999.

(51) Int. Cl.
*A61B 5/055* (2006.01)

(52) U.S. Cl. .................. 600/420; 424/9.3; 324/307; 324/309

(58) Field of Classification Search .............. 600/420; 324/307, 309; 424/9.3–9.37
See application file for complete search history.

(56) References Cited

U.S. PATENT DOCUMENTS

| | | | |
|---|---|---|---|
| 5,050,609 | A | 9/1991 | Balaban et al. |
| 5,639,906 | A | 6/1997 | London et al. |
| 6,023,634 | A | 2/2000 | Hanawa et al. |
| 2002/0127182 | A1 | 9/2002 | Sherry et al. |

FOREIGN PATENT DOCUMENTS

| | | |
|---|---|---|
| EP | 0 095 124 A1 | 11/1983 |
| EP | 0 122 000 A2 | 10/1984 |
| EP | 0 368 429 A2 | 5/1990 |
| EP | 1 331 012 A1 | 7/2003 |
| WO | WO 95/17910 | 7/1995 |
| WO | WO 98/39664 | 9/1998 |
| WO | WO 99/55670 | 11/1999 |

OTHER PUBLICATIONS

Database WPI, Section CH, Week 200017, Derwent Publications Ltd., London, GB; AN 2000-195204, XP002161319 and WO 00/06207 A (Nippon Mediphysics Co. Ltd.), Feb. 10, 2000 abstract.
Budavari et al., Merck Index, CD-ROM XP002176801, Merck & Co., Inc., Whitehouse Station, New Jersey, Monograph No. 3849, 1997.

*Primary Examiner*—Ruth S. Smith
(74) *Attorney, Agent, or Firm*—Klarquist Sparkman, LLP

(57) ABSTRACT

Method for determining in vivo concentration of a metabolite that includes administering a contrast agent to a subject, allowing the contrast agent to disperse to tissue of interest, performing CEDST MRI analysis of the subject, and comparing the results to known in vitro results to determine metabolite concentration.

10 Claims, 10 Drawing Sheets

METHOD FOR DETERMINING IN VIVO CONCENTRATION OF A METABOLITE

PRIORITY CLAIM

This application is a divisional of U.S. patent application Ser. No. 09/959,138, filed Oct. 17, 2001, (now U.S. Pat. No. 6,963,769 issued Nov. 8, 2005) which was the National Stage of International (PCT) Application No. PCT/US00/10878, filed Apr. 20, 2000, which claims the benefit of U.S. Provisional Application No. 60/130,532, filed Apr. 21, 1999, all of which are incorporated herein by reference.

FIELD

The present invention concerns a method for enhancing the quality (e.g., contrast) of images produced by magnetic resonance imaging, particularly images produced in vivo, using chemical exchange dependent saturation transfer and contrast agents.

BACKGROUND

Magnetic resonance imaging (MRI) provides a method for non-invasively obtaining diagnostic images of the body. MRI is now an indispensable diagnostic tool, and methods for improving the quality of the image produced are needed to facilitate image interpretation and provide additional diagnostic information.

A. External Contrast Agents

Conventional MRI images of biological tissues reflect a combination of spin-lattice (T1) and spin-spin (T2) water proton relaxation. Externally administered contrast agents, which enhance the relaxation rate of water protons, have been developed to enhance natural MRI contrast. Commonly used external contrast agents include paramagnetic chelated metal ions, such as gadolinium diethylenetriaminepentaacetic acid (Gd-DTPA) and chelated metal Gd-DOTA. Casali et al., *Acad. Radiol.*, 5:S214-8, (1998). The usefulness of these metal chelates as contrast agents for in vivo imaging is substantially limited by toxicity and T2 effects.

As an alternative to metal ions, other external MRI contrast agents, including iopamidol, arginine, serine and glycine, have been examined for their ability to enhance contrast in vitro. Aime et al., *Invest. Radiol.*, 23:S267-70 (1988). These external contrast agents enhance MRI contrast by decreasing the T2 signal, which is not very specific and can be influenced by many factors.

B. Saturation Transfer

Previous studies showed that by saturating protons of small metabolites (i.e. ammonia) that can undergo chemical exchange with other materials, such as water, an associated decrease in the intensity of the water proton signal resulted in a several-order magnitude increase in sensitivity compared to direct detection. Wolff and Balaban, *J. Magn. Reson.*, 86:164 (1990). This observation demonstrated that proton exchange can be imaged using saturation transfer methods in vitro.

Proton chemical exchange between water and metabolites is a common process in biological tissues. Metabolite/water proton chemical exchange can range from fast-to-intermediate-to-slow, depending on the chemistry of the exchange sites, temperature, pH and other factors. Strategies have been presented to image the distribution of chemical exchange using saturation transfer (ST) in the magnetization preparation period of an imaging sequence. Hsieh and Balaban, *J. Mag. Res.*, 74: 574 (1987); McFarland et al., *Mag. Reson. Imag.*, 6:507 (1988); Wolff and Balaban, *J. Magn. Reson.*, 86:164 (1990). ST is most effective under slow-to-intermediate exchange conditions where the exchanging spins can be adequately resolved and sufficient exchange occurs between the molecules, relative to T1, to detect transfer of the saturated protons. This limitation reduces the number of reactions that can be detected with ST; however, it may improve the specificity of the measurement in complex biological tissues.

C. Intrinsic Tissue Contrast and ST

Saturation transfer methods known prior to the present invention rely primarily on the patient's intrinsic macromolecules as the sole source of bound protons. The presence of ethanol also has been used to provide for an alternative source of bound protons. Govindaraju et al., *Alcohol and Alcoholism*, 32(6):671-681 (1997); Meyerfhoff et al. *Alcoholism: Clinical and Experimental Research*, 20(7):1283-1288 (1996). The effect observed by these authors is due to dipolar interactions between water protons and free ethanol protons, not chemical exchange. Distinguishing bound protons from free protons in vivo is complex, making irradiation of solely bound protons difficult. In addition, although the intrinsic macromolecules of some tissues readily undergo proton chemical exchange, other tissues do not. These factors have limited MRI contrast enhancement.

Nevertheless, intrinsic tissue contrast and saturation transfer have been used for imaging. For example, Balaban et al., U.S. Pat. No. 5,050,609, which is incorporated herein by reference, describes using saturation transfer to enhance MRI contrast of tissues, polymers and geological samples. Wolff and Balaban demonstrated exchange between irradiated bound protons with free protons using MRI saturation transfer methods in vivo. Wolff and Balaban *Magn. Reson. Med.*, 10:135-144 (1989). The maximum amount of decrease observed in the free proton pool was 70%. This decrease was observed only in certain tissues, such as the rabbit kidney. Kajander et al. observed the greatest MRI contrast enhancement in striated muscle, but only modest enhancement in the liver, kidney cortex and spleen. Kajander et al., *Magn. Reson. Imag.*, 4:413-7 (1996). Thomas used saturation transfer to improve the details of small vessel angiography to increase the contrast of breast and brain lesions, and to provide greater details of the knee and cervical spine. Thomas, *Radiol. Technol.*, 67:297-306 (1996).

SUMMARY

Intrinsic tissue contrast and saturation transfer has been used for imaging. Due to the amount of proton transfer in the kidney medulla, both the MRI signal and sensitivity increased, which enhanced the MRI contrast of the kidney medulla. Guivel-Scharen et al., *J. Magn. Reson.*, 133:36-45 (1998). However, no MRI contrast enhancement was observed when the intrinsic molecules of the liver and brain were used. Therefore, despite these previous methods, there still is a need for methods for enhancing the quality of images produced by MRI to facilitate image interpretation and provide additional diagnostic information.

The method of the present invention is useful for enhancing the contrast of MRI images, including images produced in vivo, using chemical exchange dependent saturation transfer (CEDST). One feature of the present invention involved identifying contrast agents which contain chemical groups having the appropriate proton exchange and chemical shift properties at physiological pH and temperature to function effectively for performing CEDST MRI analyses in vivo. One embodiment of the method comprises administering at least one contrast agent to a subject (for example mammals, such as humans) in amounts effective to perform CEDST MRI analysis, and thereafter performing CEDST MRI analysis to produce an image of the subject.

There currently are two working embodiments for performing CEDST MRI analysis. A first embodiment comprised: (a) selectively irradiating and saturating an exchangeable proton or protons on an exogenously administered molecule with an applied magnetic field; and (b) determining the effect of this saturation on the water proton MR signal amplitude. Transfer of saturated protons reduces the water proton signal amplitude. The distribution of this effect within a sample or subject is determined using conventional MRI imaging methods for determining topology of the water proton MR signal amplitude.

A second working embodiment for performing CEDST MRI analysis comprises: (a) selectively irradiating and saturating an exchangeable proton or protons on an exogenously administered molecule with an applied magnetic field; (b) applying a selective irradiation with an equal but opposite $\Delta\omega CA$ from the water proton resonance position, thereby providing a first image set with the irradiation $\pm\Delta\omega_{CA}$; (c) producing a second image set by either (1) subtracting or (2) dividing the images of the set (i.e., $+\Delta\omega_{CA}$ and $-\Delta\omega_{CA}$) to minimize the effects of macromolecular interference, T2, T1 and irradiation field in-homogeneity.

The contrast agent can be administered as a solid, as a dispersion or solution, such as an aqueous composition, as a mixture of two or more agents, etc. Intravenous (IV) delivery of a contrast agent or agents dissolved or suspended in a physiologically acceptable carrier or carriers is one method which can be used for administering contrast agents.

Examples of contrast agents suitable for administration as exogenous contrast agents for performing CEDST MRI analyses in vivo can be selected from the group consisting of: sugars, including oligosaccharides and polysaccharides, such as dextran; amino acids, such as 5-hydroxy-tryptophan (which also includes an indole —NH having a pKa of about 1.7) and including oligomers of amino acids and proteins; nitrogen-containing heterocycles generally; indoles, purines and pyrimidines; nucleosides; imidazole and derivatives thereof, such as 2-imidazolidone and 2-imidazoldinethione; imino acids, including azetidines, such as azetidine-2-carboxylic acid, pyrolidines, such as 4-trans-hydroxy-proline, and piperidines, such as pipecolinic acid; barbituric acid and analogs thereof, such as 2-thio-barbituric acid and 5,5-diethylbarbituric acid; miscellaneous materials, such as guanidine, hydantoin, parabanic acid, and biologically active salts thereof; and mixtures of these contrast agents.

Suitable contrast agents often include at least one functional group bearing a proton capable of chemical exchange. Examples of these functional groups include, without limitation, amides, amines, carboxyls, hydroxyls, and sulfhydryls.

In addition to being useful for obtaining images by CEDST MRI having substantially enhanced contrast compared to conventional MRI methods, the present method also is useful for determining certain conditions, such as pH and temperature, both in vitro and in vivo. One embodiment of a method for determining pH comprised first determining, by CEDST MRI, a ratio of $(M_O-M_S)^{Site\ 1}/(M_O-M_S)^{Site\ 2}$ for a contrast agent having two exchangeable protons, and thereafter comparing the $(M_O-M_S)^{Site\ 1}/(M_O-M_S)^{Site\ 2}$ ratios to a standard curve to determine pH of the desired tissue. A working embodiment of the method used dihydrouracil as the contrast agent, which was provided as an aqueous composition having about 62.5 mM contrast agent. A standard pH curve was prepared by performing in vitro CEDST MRI analyses of dihydrouracil as a function of pH. Ratios of $(M_O-M_S)^{Site\ 1}/(M_O-M_S)^{Site\ 2}$ were then plotted to generate the standard curve.

In yet another embodiment of the present invention, two or more contrast agents are used to determine pH both in vitro and in vivo. This method provided a greater dynamic range to the measurement. The method comprised first determining, by CEDST MRI, a ratio of $M_S^{Site\ 2}(M_O-M_S)^{Site\ 1}/[M_S^{Site\ 1}(M_O-M_S)^{Site\ 2}]$ for one or more contrast agents having two exchangeable protons, and thereafter comparing the $M_S^{Site\ 2}(M_O-M_S)^{Site\ 1}/[M_S^{Site\ 1}(M^O-M_S)^{Site\ 2}]$ ratios to a standard curve to determine pH of the desired tissue. Working embodiments of the method used either dihydrouracil or a combination solution of 5-Hydroxytryptophan and 2-Imidazolidinethione as the contrast agent, which was provided as an aqueous composition having about 62.5 mM of each chemical in the solution. Mixtures of other contrast agents may also be used to practice the present invention. The contrast agents may be in the form of polymers. A standard pH curve is prepared by performing in vitro CEDST MRI analyses of the contrast agent. Ratios of $M_S^{Site\ 2}(M_O-M_S)^{Site\ 1}/[M_S^{Site\ 1}(M_O-M_S)^{Site\ 2}]$ are plotted to generate the standard curve. To determining pH of physiological tissues in vivo, a standard curve is generated as described, and the one or more contrast agents are administered to a subject, allowing the one or more contrast agents sufficient time to locate in tissue of interest, determining in vivo by CEDST MRI analysis a ratio of $M_S^{Site\ 2}(M_O-M_S)^{Site\ 1}/[M_S^{Site\ 1}(M_{O-MS})^{Site\ 2}]$ using the one or more contrast agents, and comparing the $M_S^{Site\ 2}(M_O-M_S)^{Site\ 1}/[M_S^{Site\ 1}(M_O-M_S)^{Site\ 2}]$ ratio to a standard curve to determine pH of the tissue. Contrast agents which can be used include 5,6-dihydrouracil, 5-hydroxy-tryptophan and 2-imidzaolidinethione, polymers thereof, and mixtures thereof.

Similar methods also can be used to determine other in vitro or in vivo characteristics, such as the concentration of a specific metabolite in solution. The metabolite concentration can be determined using a contrast agent having exchangeable protons that are affected by the presence of the metabolite. Like the pH determination described above, where protons on the contrast agent were affected by changes in the free proton concentration, the $(M_O-M_S)^{Site\ 1}/(M_O-M_S)^{Site\ 2}$ ratio can be used to determine the metabolite concentration. This ratio can be determined in vivo by CEDST MRI analysis, and the determined value compared to a standard curve to determine the concentration of the metabolite in the sample tested. A working embodiment of the method for determining phosphate concentration used dihydrouracil as the contrast agent, which was provided as an aqueous composition having about 62.5 mM contrast agent at a fixed pH=6. A standard phosphate curve was prepared by performing in vitro CEDST analyses of dihydrouracil as a function of phosphate concentration. Ratios of $(M_O-M_S)^{Site\ 1}/(M_O-M_S)^{Site\ 2}$ were then plotted to generate the standard phosphate curve. In a like manner, the concentration of other metabolites, such as acetate and carbonate can be determined using the method of the present invention.

The present invention also provides a method for determining physiological temperature. One embodiment of the method for determining physiological temperature comprised first performing CEDST MRI analysis in vivo, and thereafter comparing the in vivo CEDST MRI results to a standard curve to determine physiological temperature. A working embodiment of the method for determining temperature used barbituric acid as the contrast agent, which was provided as an aqueous composition having about 62.5 mm contrast agent. However, other contrast agents which are temperature sensitive can also be used. A standard temperature curve was prepared by performing in vitro CEDST analyses of barbituric acid, at fixed pH and phosphate concentration, as a function of temperature. The shape of the spectrum changes with changes in temperature. This shape can be characterized through a line-shape analysis of the entire ST spectrum, or of a subset of the spectrum, as a function of temperature to derive the standard temperature calibration curve. A contrast agent possessing two proton chemical exchange sites can also be used to determine temperature, like the pH and phosphate measurements, by the ratio of $(M_O-M_S)^{Site\ 1}/(M_O-M_S)^{Site\ 2}$ as a function of temperature.

The foregoing and other objects, features, and advantages of the invention will become more apparent from the following detailed description of several embodiments with reference to the accompanying figures.

DETAILED DESCRIPTION

Figure 1:
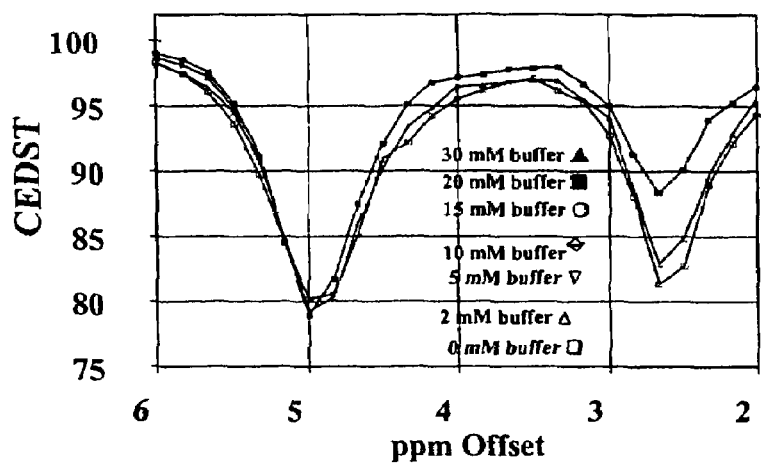
FIG. 1 is a CEDST spectra ($M_S$ versus offset, in ppm) of 62.5 mM 5,6-dihydro-uracil, containing 0-30 mM, pH 6 phosphate buffer, illustrating the effect of buffer concentration on the image produced by the two exchangeable protons of 5,6-dihydrouracil at 2.67 ppm and 5.00 ppm.

The following definitions and methods are provided to better define the present invention and to guide those of ordinary skill in the art in the practice of the present invention. It must be noted that as used herein and in the appended claims, the singular forms "a" or 'an' or "the" include plural referents unless the context clearly dictates otherwise. Thus, for example, reference to "a contrast agent" includes a plurality of such agents and includes reference to one or more agents and equivalents thereof known to those skilled in the art, and so forth.

I. Introduction

The present invention provides a method for obtaining MR images, particularly in vivo images, where the images provide better contrast, and therefore better quality, than prior known methods. Features of a working embodiments of the invention include some or all of the following: selecting one or more appropriate contrast agents; administering a contrast agent or agent, or composition comprising the contrast agent or agents, to a subject; irradiating protons of the contrast agent at a predetermined frequency ($+\Delta\omega_{CA}$) off the water peak, and thereafter providing an image; irradiating at a predetermined frequency ($-\Delta\omega_{CA}$) off the water peak, and providing a second image; and determining a third image provided by the subtraction or ratio of the first image relative to the second image. Contrast agents useful for practicing the invention, and one embodiment of a method for obtaining in vivo MR images using such contrast agents, are described in more detail below.

II. Definitions

The following terms are provided solely to aid in the understanding of this invention. These definitions should not be construed to have a scope less than would be understood by a person of ordinary skill in the art.

Amino Acid: An organic acid in which the carbon atoms in the hydrocarbon portion carry an amino group.

Chemical Exchange: A physical process whereby nuclides initially bound to a first compound become bound to a second compound, and hence are physically transferred from the first to the second compound.

Chemical Exchange Dependent Saturation Transfer (CEDST): Refers to all saturation transfer processes between molecules that are dependent on chemical exchange between the molecules.

Contrast Agent: A genus of materials having at least one proton that can chemically exchange for protons of another material, and which can be used to perform CEDST imaging.

Functional Group: A group of atoms, generally including a heteroatom such as oxygen, sulfur or nitrogen, bonded to one or more carbon atoms, to which an exchangeable proton also is attached (e.g., functional groups such as amines, hydroxyls or sulfhydryls) or which renders a proton attached to an adjacent atom more acidic (e.g., a proton bonded to a carbon atom a to a carbonyl carbon). Examples of functional groups include, but are not limited to: amines (—$R_3N$, where R generally is an alkyl group, an acyl group or hydrogen;, amides (—RCON—, where R generally is an alkyl group or hydrogen); carbonyl groups [e.g., ketones ($R_2C=O$) and aldehydes (RHC=O)]; sulfhydryls (—SH); etc.

Magnetization Transfer (MT): Refers to through-space dipolar interactions of nuclides within or between molecules.

MRI: Magnetic resonance imaging is a noninvasive diagnostic process that uses an MR scanner to obtain images of objects, tissues, or bodies. An MR scanner uses nuclear magnetic resonance to obtain images. The MR scanner includes (1) a body-encircling magnet that generates a strong, uniform magnetic field which interacts with radio waves to excite the nuclei of specific atoms, such as hydrogen, and (2) a detector that detects relaxation of the nuclei and transforms the detected signals into a visual image.

Mammals: Members of the Class Mammalia.

Pharmaceutically Acceptable Carriers: Includes all known pharmaceutically acceptable carriers such as those described in Remington's *Pharmaceutical Sciences*, by E. W. Martin, Mack Publishing Co., Easton, Pa., 15th Edition (1975), herein incorporated by reference, which describes compositions and formulations suitable for pharmaceutical delivery of the contrast agents herein disclosed. Embodiments of the invention comprising one or more contrast agents can be prepared with conventional pharmaceutically acceptable carriers, adjuvants and counterions as would be known to those of skill in the art.

In general, the nature of the carrier will depend on the particular mode of administration being employed. For instance, parenteral formulations usually comprise, in addition to the one or more contrast agents, injectable fluids that include pharmaceutically and physiologically acceptable fluids, including water, physiological saline, balanced salt solutions, buffers, aqueous dextrose, glycerol, ethanol, sesame oil, combinations thereof, or the like as a vehicle. The medium also may contain conventional pharmaceutical adjunct materials such as, for example, pharmaceutically acceptable salts to adjust the osmotic pressure, buffers, preservatives and the like. The carrier and composition can be sterile, and the formulation suits the mode of administration.

For solid compositions (e.g., powder, pill, tablet, or capsule forms), conventional non-toxic solid carriers can include, for example, pharmaceutical grades of mannitol, lactose, starch, sodium saccharine, cellulose, magnesium carbonate, or magnesium stearate. In addition to biologically-neutral carriers, pharmaceutical compositions to be administered can contain minor amounts of auxiliary substances, such as wetting or emulsifying agents, preservatives, and pH buffering agents and the like, for example sodium acetate or sorbitan monolaurate.

The composition can be a liquid solution, suspension, emulsion, tablet, pill, capsule, sustained release-formulation, or powder. The composition can be formulated as a suppository, with traditional binders and carriers such as triglycerides.

Saturation Transfer (ST): "Saturation" refers to the destruction or randomization of the net magnetization in a sample using an applied magnetic field with or without spatial magnetic field gradients. Transfer refers to a physical process whereby this saturation is passed between different molecules by through-space interactions or direct chemical exchange from a first compound to a second compound.

Subject: Living multicellular vertebrate organisms, a category which includes human and veterinary subjects, for example mammals; farm animals such as pigs, horses, and cows; laboratory animals such as rodents and rabbits; birds, and primates.

$\Delta\omega_{CA}$: Refers to the chemical shift difference between the contrast agent proton chemical exchange site and the water proton resonance frequency.

See, Balaban et al., U.S. Pat. No. 5,050,609, and Balaban et al., "Detection of Proton Chemical Exchange Between Metabolites and Water in Biological Tissues," *J. Magn. Res.,*" 133:36-45 (1998), which are incorporated herein by reference, for further information concerning MRI and ST.

III. Contrast Agents

One feature of the present invention is the identification/selection of one or more appropriate contrast agents, that can be used to enhance the contrast of an image of a material produced by MRI. The phrase "contrast agent" describes a genus of materials. Contrast agents typically have functional groups that provide (1) appropriate proton exchange, and (2) MRI chemical shift properties at physiological pH and temperature to function effectively for performing in vivo CEDST MR imaging.

A several thousand-fold enhancement of the proton signal can result via a reduction in the water signal ($M_S/M_O$) based on Equation 1.

$$M_S/M_O=[1/(1+k_{CA}T_{1W})] \qquad \text{Equation 1}$$

With reference to Equation 1, $M_S$ is the magnitude of the water proton signal in the presence of contrast agent proton saturation; $M_O$ is the magnitude of the signal under control irradiation at the opposite frequency offset; $k_{CA}$ is the site proton exchange rate constant; and $T_{1W}$ is the spin lattice relaxation rate of water protons. Guivel-Scharen et al., *J. Magn. Res.*, 133:36 (1998). The site proton lifetime, $\tau_{CA}$, is the amount of time protons undergoing chemical exchange remain bound to a particular molecule and is the inverse of the site proton chemical exchange rate constant, $k_{CA}$. Therefore, $$k_{CA}=1/\tau_{CA} \qquad \text{Equation 2}$$

The amount of water affected per exchange site is similar to that in metal-based T1 agents since both depend on the site proton lifetime, $\tau_{CA}$, and the diffusion rate of protons over the T1 time of water.

Factors that can be considered to select a contrast agent include: (1) the exchange rate, $k_{CA}$, (the inverse of $\tau_{CA}$), is in the slow-to-intermediate exchange rate domain, which is defined as:

$$\tau_{CA}\Delta\omega_{CA}>1 \qquad \text{Equation 3}$$

where $\Delta\omega_{CA}$ is the chemical shift difference (in radians/second) between the site and water, and $\tau_{CA}$ is the site proton lifetime [Dwek, *Nuclear Magnetic Resonance (N.M.R.) in Biochemistry, Applications to Enzyme Systems*, Oxford UK, (1973)]; (2) the $\Delta\omega_{CA}$ is large enough to support a large $k_{CA}$ while satisfying the condition of Equation 3 where $\Delta\omega_{CA}>k_{CA}$; (3) a large $\Delta\omega_{CA}$ also is desirable for specificity since the $B_O$ inhomogeneity can be >2 ppm; (4) high solubility in aqueous, biologically acceptable carriers; (5) low toxicity; and (6) delivery of the contrast agent to a predetermined/selected tissue after administration.

Examples of classes of materials found to be useful in working embodiments of the present invention for administration as exogenous contrast agents include, but are not limited to, amino acids, sugars, nucleosides and their pyrimidine and purine bases, barbituric acid and analogs thereof, nitrogen-containing heterocycles, including heterocycles having plural exchangeable protons, such as two or more —NH groups, and heterocycles having plural ring systems, imidazole and analogs thereof, and imino acids and analogs thereof.

Examples of amino acids useful as exogenously administered MRI contrast agents include alanine, arginine, lysine, glutamine, tryptophan, and 5-hydroxy-tryptophan. The amino acids used all were of the L configuration, but amino acids having the D configuration also work to practice the method of the present invention. All stereoisomers of contrast agents discussed herein can be used to perform CEDST imaging. 5-hydroxy-tryptophan has been used in working embodiments for in vivo imaging, as discussed in more detail below with reference to Table 1.

Monosaccharides, sugars, oligosaccharides (e.g., disaccharides such as sucrose and lactose), polysaccharides, as well as the ketone and aldehyde analogs of such sugars, such as mannitol and sorbitol, are useful for administration as contrast agents for practicing the method of the present invention. Examples of sugars used to practice working embodiments of the present invention include, without limitation, mannitol, mannose, sorbitol, sorbose, fructose, dextrose, galactose, sucrose, maltose and lactose. Structural formulas for certain of these sugars and the disaccharide sucrose are provided below. All hydroxylprotons (indicated in bold) of the sugars potentially are involved in the proton chemical exchange, and hence all hydroxylprotons of the sugars are irradiated.

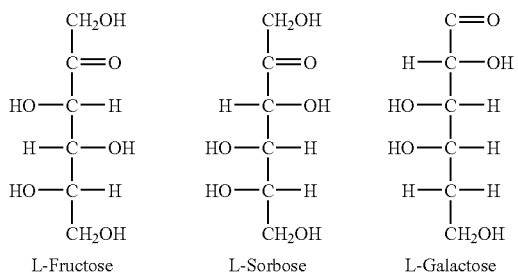

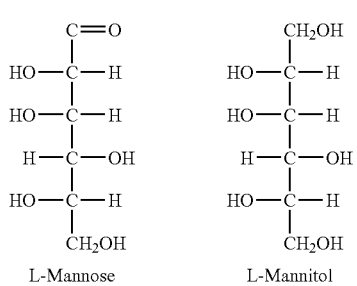

Sugars

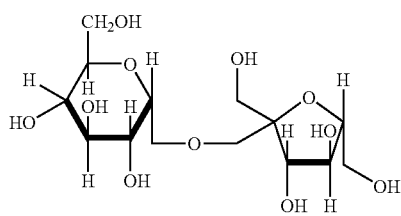

Sucrose

Examples of nucleosides and their pyrimidine and purine bases that are useful as contrast agents for performing CEDST MRI include 5,6-dihydrouracil, uridine and thymidine.

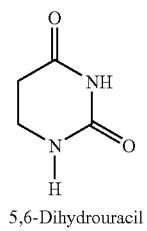

5,6-Dihydrouracil

-continued

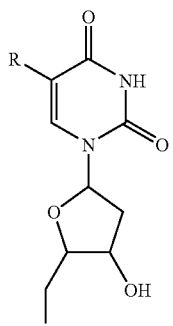

Thymidine: R = CH₃
Uridine: R = H

Barbituric acid and analogs thereof also are useful for exogenous administration as contrast agents.

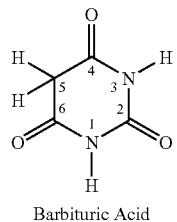

Barbituric Acid

Suitable barbituric acid analogs typically have general structural Formula 1.

Formula 1

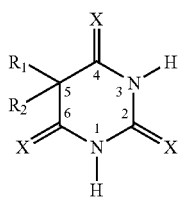

With reference to Formula 1, $R_1$ and $R_2$ are independently selected from the group consisting of hydrogen and lower alkyl, where "lower" refers to hydrocarbon chains having 10 or fewer carbon atoms in the chain, and X is selected from the group consisting of oxygen and sulfur. 2-thio-barbituric acid and barbital (5,5-diethylbarbituric acid) are examples of barbituric acid analogs used to perform CEDST MRI according to the method of the present invention.

Imino acids also are useful as contrast agents for CEDST MRI. Imino acids, such as (1) azetidines, e.g., azetidine-2-carboxylic acid,

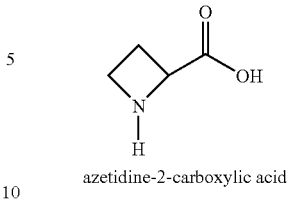

azetidine-2-carboxylic acid (2) pyrrolidines, e.g., 4-trans-hydroxy-proline,

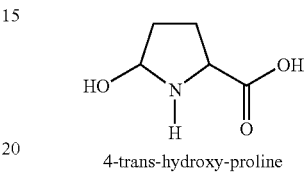

4-trans-hydroxy-proline and (3) piperidines, e.g., pipecolinic acid,

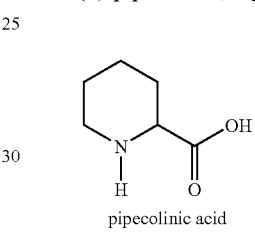

pipecolinic acid have been used as contrast agents in working embodiments of the present invention.

The heterocyclic compounds, which includes indoles, generally, and the —NH site on the indole ring of 5-hydroxy-tryptophan, have both a maximal ($M_O$–$M_S$) in the physiological range and a desirable chemical shift ($\geq 5$ ppm), and thus remain in slow-to-intermediate exchange at physiological pH. Both these features may be the result of the heterocyclic structure of these chemicals. The effect of the heterocyclic ring is to redistribute electrons within the ring, which can substantially affect the shielding of all nuclei attached to the ring, and increase the ppm offset of those nuclei which are less shielded.

Polymeric forms of contrast agents can provide better results for in vivo administration as opposed to the monomeric precursors. One example is the polymerization of sugars into dextran. As seen in Table 1, dextran maintains the exchangeable site of the sugars despite being polymerized. One advantage of polymerizing contrast agents is the delivery of more exchange sites per osmotically active particle compared to the monomer. This may have important advantages in biological applications where the osmolality of the contrast agent solution is important to reduce side effects.

Combinations of contrast agents also can be used, including combinations within a class of agents, such as a combination of sugars, and combinations between two or more classes of contrast agents, such as an amino acid or a protein and a sugar or oligosaccharide. Examples of combinations used in a working embodiment of the present invention comprised combinations of thymidine (thymidine+pentose sugar) or uridine (uracil+pentose sugar) and phosphate, in addition to 5-hydroxy-tryprophan and 2-imidazolidinethione.

Compositions comprising contrast agents, and combinations of contrast agents, also can be made to practice the method of the present invention. For example, contrast agents and pharmaceutically acceptable carriers, materials for other diagnostic analyses, therapeutics, and combinations of these materials, can be combined to provide a composition useful for administration to a subject to practice the method of the present invention.

Additional information concerning contrast agents, data collected using such agents, and the methods used to obtain such data, is provided in the Examples below and Table 1.

Contrast agents can be made to target a particular tissue. This can be accomplished by, for example, conjugating a tumor-specific antibody or ligand to a contrast agent(s) or polymers thereof, or by generating polymers that remain in the vasculature for angiography.

IV. Administering Contrast Agents

Once one or more appropriate contrast agents are selected, and such agent or agents is administered to a subject. Known methods for administering therapeutics and diagnostics can be used to administer contrast agents for practicing the present invention. For example, fluids that include pharmaceutically and physiologically acceptable fluids, including water, physiological saline, balanced salt solutions, buffers, aqueous dextrose, glycerol or the like as a vehicle, can be administered by any method used by those skilled in the art. Methods of introduction include, but are not limited to, intradermal, intramuscular, intraperitoneal, intravenous, subcutaneous, intranasal, rectal, vaginal, and oral routes. The compositions may be administered by any convenient route, for example by infusion or bolus injection, by absorption through epithelial or mucocutaneous linings (e.g., oral mucosa, vaginal, rectal and intestinal mucosa, etc.) and may be administered together with other biologically active agents. Administration can be systemic or local. In addition, the contrast agent(s) compositions may be introduced into the central nervous system by any suitable route, including intraventricular and intrathecal injection; intraventricular injection may be facilitated by an intraventricular catheter, for example, attached to a reservoir, such as an Ommaya reservoir. Solid compositions can be administered in the form of powders, pills, tablets, capsules, etc. The present invention also provides pharmaceutical compositions which include contrast agents, alone or with a pharmaceutically acceptable carrier. In one example, homogeneous compositions of the one or more contrast agents includes compositions that are comprised of at least 90% of the contrast agents in the composition.

Amounts of the one or more contrast agents sufficient to provide good CEDST MRI results will be used, balanced by other considerations such as whether the contrast agent used for a particular application might produce undesirable physiological results. The precise dose to be employed in the formulation can also depend on the route of administration, and should be decided according to the judgment of the practitioner and each subject's circumstances. In addition, in vitro assays (such as those disclosed herein in the following Examples) may optionally be employed to help identify optimal dosage ranges. Effective doses may be extrapolated from dose-response curves derived from in vitro or animal model test systems. Examples of doses that can be administered to a subject includes doses in the range of 0.0006-0.05 moles of contrast agent(s)/kg of subject.

Contrast agents have been used successfully in concentrations ranging from about 0.2 mM (such as with dextran) to about 250 mM (such as with the sugars). Thus, the amounts of the contrast agent or agents administered can range from moles, but more likely will be used in millimolar-to-micromolar amounts. Polymerization of an agent, or copolymers of various agents, significantly increases the number of exchange sites while reducing the overall concentration of the agent itself.

Delivery Systems

Such carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate.

The invention also provides a pharmaceutical pack or kit comprising one or more containers filled with one or more of the ingredients of the pharmaceutical contrast agent(s) compositions. Optionally associated with such container(s) can be a notice in the form prescribed by a governmental agency regulating the manufacture, use or sale of pharmaceuticals or biological products, which notice reflects approval by the agency of manufacture, use or sale for human administration. Instructions for use of the composition can also be included.

The pharmaceutical compositions or methods of treatment may be administered in combination with other therapeutic treatments, such as other antineoplastic or antitumorigenic therapies.

V. Irradiating Protons of the Contrast Agent at a Predetermined Frequency to Reduce the Intensity of the MRI Signal Once an appropriate contrast agent or agents have been selected, the agents are administered to the subject and allowed to arrive at the tissue/region of interest. The subject is then analyzed by CEDST MRI analysis to produce an image of the subject. There currently are two working embodiments for performing ST MRI analysis. A first embodiment comprised: (a) selectively irradiating and saturating an exchangeable proton or protons on an exogenously administered agent with an applied magnetic field; and (b) determining the effect of this saturation on the water proton MR signal amplitude. Transfer of saturated protons reduces the water proton signal amplitude. The distribution of this effect within a sample or subject is determined using conventional MRI imaging methods for determining topology of the water proton MR signal amplitude.

A second working embodiment for performing CEDST MRI analysis comprised: (a) selectively irradiating and saturating an exchangeable proton or protons on an exogenously administered agent with an applied magnetic field; (b) applying a selective irradiation with an equal but opposite $\Delta\omega_{CA}$ from the water proton resonance position, thereby providing an image set with the irradiation $\pm\Delta\omega_{CA}$; (c) producing an image set by either (1) subtracting or (2)

dividing the images of the set (i.e., $+\Delta\omega_{CA}$ and $-\Delta\omega_{CA}$) to minimize the effects of macromolecular interference, T2, T1 and irradiation field in-homogeneity. The final image has the greatest contrast (brightness) in regions containing the external contrast agent, as a result of decreasing the intensity of the water peak.

The following examples are provided to illustrate certain features of working embodiments of the present invention. The scope of the invention should not be limited to those features exemplified.

EXAMPLE 1

This example describes the methods and results of in vitro studies conducted to characterize the proton chemical exchange of several compounds with water. Candidate compounds (Table 1) were screened to identify those containing proton chemical exchange sites with large $\Delta\omega_{CA}$, high solubility and appropriate chemical exchange rates at physiological pH and temperature (pH 7.4 and 37° C.). Test compounds were dissolved in HPLC grade water at concentrations denoted in Table 1 with inorganic phosphate buffers to maintain pH. Gomori, *Methods Enzymol.*, 1:143, 1955. All chemicals were obtained from commercial sources (Aldrich Chemical Co., Milwaukee, Wis.; Mallinckrodt Specialty Chemical Co., Paris, Ky.; and Sigma Chemical Co., St. Louis, Mo.).

Phosphate buffer concentration affected chemical exchange rates as previously described. Liepinsh and Otting, *Magn. Reson. Med.*, 35:30, 1995. FIG. 1 shows the CEDST spectra of 5,6-dihydro-uracil solutions containing varying phosphate buffer concentrations. Two specific proton chemical exchange sites are visible for 5,6-dihydro-uracil; one at 5.00 ppm and one at 2.67 ppm. The site at 2.67 ppm was significantly affected by changes in phosphate concentration; as the phosphate concentration increased, the $M_S$ value increased, indicating that less exchange was occurring. The site at 5.00 ppm was substantially unaffected by changes in phosphate concentration. Therefore, the phosphate concentration was held constant at 20 mM for the results reported in Table 1 to control for these effects.

TABLE 1

Compounds Tested as Potential Contrast Agents.

| Compound[1] | Conc (mM) | Functional Group | ppm[2] | pH[3] | $\frac{Ms}{Mo}$ | Mo − Ms (%) |
|---|---|---|---|---|---|---|
| Sugars[4]: | | Hydroxyl protons (—OH) | | | | |
| Mannitol | 250 mM | —OH | 1.000 | 7.0 | 0.89 | 9.0 |
| Sorbitol | 250 mM | —OH | 1.000 | 7.0 | 0.88 | 7.3 |
| Fructose | 250 mM | —OH | 1.333 | 7.0 | 0.88 | 9.3 |
| Dextrose | 250 mM | —OH | 1.500 | 7.0 | 0.89 | 8.7 |
| Galactose | 250 mM | —OH | 1.167 | 7.0 | 0.85 | 10.3 |
| Sucrose | 250 mM | —OH | 1.333 | 7.0 | 0.86 | 10.2 |
| Maltose | 250 mM | —OH | 1.500 | 7.0 | 0.79 | 14.8 |
| Lactose | 250 mM | —OH | 1.333 | 7.0 | 0.68 | 20.9 |
| Dextran5 | | | | | | |
| 1.75 gm/100 ml | 0.25 mM | —OH | 0.833 | 7.0 | 0.84 | 11.1 |
| 3.50 gm/100 ml | 0.5 mM | —OH | 1.167 | 7.0 | 0.91 | 8.1 |
| 7.00 gm/100 ml | 1.0 mM | —OH | 1.167 | 7.0 | 0.81 | 13.6 |
| 14.0 gm/100 ml | 2.0 mM | —OH | 1.167 | 7.0 | 0.76 | 18.9 |
| Amino Acids[6]: | | Amino protons (—NH$_2$) | | | | |
| L-Alanine | 125 mM | —NH$_2$ | 3.000 | 4.0 | 0.36 | 67.4 |
| L-Arginine | 125 mM | —NH$_2$ | 3.000 | 4.0 | 0.36 | 65.8 |
| L-Arginine | 125 mM | Guanidinium Protons | 2.000 | 5.0 | 0.33 | 57.7 |
| L-Lysine | 125 mM | —NH$_2$ | 3.000 | 4.0 | 0.34 | 66.2 |
| L-Glutamine | 125 mM | —NH$_2$ | 2.000 | 5.2 | 0.70 | 27.6 |
| L-Tryptophan | 35 mM | —NH$_2$ | 2.000 | 6.5 | 0.89 | 12.2 |
| 5-Hydroxy-Tryptophan[7] | 62.5 mM | —NH$_2$ | 2.833 | 4.0 | 0.57 | 41.6 |
| | | Indole ring —NH | 5.333 | 8.0 | 0.79 | 21.2 |
| Nucleosides and their pyrimidine and purine bases[7]: | | Base protons (—NH) | | | | |
| 5,6 Dihydrouracil | 62.5 mM | 3-NH | 5.000 | 6.0 | 0.78 | 22.2 |
| 5,6 Dihydrouracil | 62.5 mM | 1-NH | 2.667 | 7.0 | 0.77 | 22.2 |
| Uridine[8] | 125 mM | 3-NH | 6.333 | 4.0 | 0.65 | 34.7 |
| Thymidine[8] | 125 mM | 3-NH | 6.333 | 5.0 | 0.65 | 34.8 |
| Barbituric Acid and its derivatives: | | Pyrimidine ring Protons (—NH) | | | | |
| Barbituric Acid[7] | 62.5 mM | —NH | 5.000 | 6.5 | 0.68 | 32.5 |
| 2-Thio-Barbituric Acid[7] | 62.5 mM | —NH | 6.333 | 5.0 | 0.65 | 35.3 |
| Barbital (5,5-Diethyl-Barbituric Acid)[7] | 62.5 mM | —NH | 5.000 | 4.0 | 0.82 | 14.2 |
| Imino Acids (their Azetidine, Pyrrolidine, and Piperidine forms) | | Base protons (—NH) | | | | |
| Pipecolinic Acid[6] | 62.5 mM | —NH | 3.33 | 5.0 | 0.81 | 19.3 |
| 4-Trans-Hydroxy-Proline[6] | 62.5 mM | —NH | 4.50 | 4.0 | 0.77 | 18.6 |
| | | —NH | 3.50 | 4.0 | 0.80 | 20.0 |

TABLE 1-continued

Compounds Tested as Potential Contrast Agents.

| Compound[1] | Conc (mM) | Functional Group | ppm[2] | pH[3] | $\frac{Ms}{Mo}$ | $\frac{Mo - Ms}{Mo}$ (%) |
|---|---|---|---|---|---|---|
| Azetidine-2-Carboxylic Acid | 62.5 mM | —NH | 3.50 | 5.0 | 0.74 | 25.5 |
| Miscellaneous: | | | | | | |
| Guanidine HCl[4] | 125 mM | Guanidinium protons | 2.000 | 7.0 | 0.38 | 60.0 |
| Hydantoin[6] | 62.5 mM | —NH | 5.667 | 4.0 | 0.81 | 18.7 |
| | | —NH | 2.833 | 6.0 | 0.78 | 21.3 |
| Parabanic Acid[6] | 62.5 mM | —NH | 5.167 | 7.0 | 0.79 | 20.5 |
| | | —NH | 3.333 | 8.0 | 0.74 | 25.4 |
| | | —NH | 2.333 | 8.0 | 0.77 | 22.5 |
| Imidazole and its derivatives: | | | | | | |
| 2-Imidazolidone[6] | | Ring protons (—NH) | 1.167 | 5.0 | 0.68 | 30.4 |
| | | Ring protons (—NH) | 1.167 | 8.0 | 0.68 | 29.8 |
| 2-Imidazolidinethione[6] | | Ring protons (—NH) | 2.833 | 4.0 | 0.79 | 20.9 |
| | | Ring protons (—NH) | 2.833 | 7.0 | 0.65 | 34.5 |

[1]All compounds were evaluated at 37° C. and were dissolved in HPLC water using a 20 mM phosphate buffer unless otherwise noted. The power level of the off-resonance saturation was $10.88 \times 10^{-7}$T.
[2]ppm listed is relative to the resonant frequency of water.
[3]The pH listed is where the greatest proton chemical exchange effect was noted, save for those solutions only evaluated at pH = 7.
[4]These compounds were evaluated at a single pH level of 7.0.
[5]Dextran molecular weigh: was approximately 70,000 gm/mole; thus, concentrations listed (mM) for these solutions are approximate.
[6]All solutions were evaluated at pH = 4, 5, 6, 7 and 8, except for L-Glutamine and L-Tryptophan.
[7]These solutions were evaluated at pH = 4, 5, 6, 7 and 8. 5,6 Dihydrouracil, 5-Hydroxy-Tryptophan, and Barbituric acid solutions were also evaluated at pH = 6.5 and 7.4.
[8]All solutions of this compound were evaluated using a 2 mM phosphate buffer. Because phosphaw is the optimal physiologic catalyst of proton chemical exchange (Liepinish and Otting, MRM 35: 30-42. 1996), the use of a 20 mM concentration increased the exchange rate observed, increased the desired exchange Ms/Mo ratio, and decreased the (Mo - Ms).

With reference to Table 1, the compound, concentration of the compound in 20 mM phosphate buffer, the protons and functional group bearing the protons being irradiated are provided. Moreover, $M_S/M_O$ and $M_O-M_S$ are methods for expressing the difference between the control and the experimental image, and hence the contrast, and is analogous to the usage in radiology. The smallest $M_S/M_O$ values, and conversely the largest $(M_O-M_S)$ values, correspond to the greatest contrast. An $M_S/M_O$ value of less than 0.80, or an $(M_O-M_S)$ value of greater than 20% currently is believed to be the minimal value to provide for good imaging contrast, although smaller values may be useful for certain applications. An example of a ppm value that can be used for imaging is about 5 ppm or greater. For in vivo imaging an example of a pH value of the maximal $(M_O-M_S)$ effect is from about 6.5 to 7.5, due to physiological conditions.

CEDST spectra were acquired at 7T using a Bruker AC-300 wide bore spectrometer at 37° C. The observation frequency was set on the water peak and the decoupler was used to provide off-resonance saturation. Studies were conducted using a steady-state with irradiation (15 seconds) over a range of irradiation frequencies±8.00 ppm from water. CEDST spectra were plotted in the form of water amplitude ($M_S$) versus irradiation frequency. Pulse sequence parameters: PW=8.0 μsec ($1.47 \times 10^{-6}$T; Flip angle=90°), one acquisition/Hz offset, 8192 data points, resolution of 0.97 Hz/pt, SW=8000 Hz.

Several classes of chemical exchange sites were evaluated (see Table 1). Sugar hydroxyl groups provided good chemical exchange sites at pH 7 ($M_S/M_O$ 0.89-0.68; 250 mM sugar). These compounds are not as useful because their $\Delta\omega_{CA}$ values (<2 ppm) are too small.

Sugar polymers, such as dextran, maintained the chemical exchange and shift properties observed with the monomeric sugars and also provided numerous exchange sites per osmole. Therefore, polymerization can be used to reduce the osmotic load.

Both the protons of the amino backbone of amino acids and the guanidinium R-group of arginine provide a good chemical exchange site with 2-3 ppm shifts (Table 1). However, these protons are not as useful because they begin fast exchange by about pH 7.0. The indole ring —NH group on amino acid 5-hydroxy-tryptophan had useful properties. This is because it possessed a $\Delta\omega_{CA}$ of 5.33 ppm and its exchange rates were suitable over the pH range of 7.0-8.0.

Additional ring-NH groups including nucleosides, their pyrimidine and purine bases, as well as derivatives of barbituric acid and imidazole, were evaluated (Table 1 and FIGS. 2-5). Several of these compounds revealed $\Delta\omega_{CA}$ values in the desirable range ($\Delta\omega_{CA}$>3.0 ppm) and $M_S/M_O$ values in the range of 0.7 for solutions at concentrations of 62.5 mM.

Figure 2:
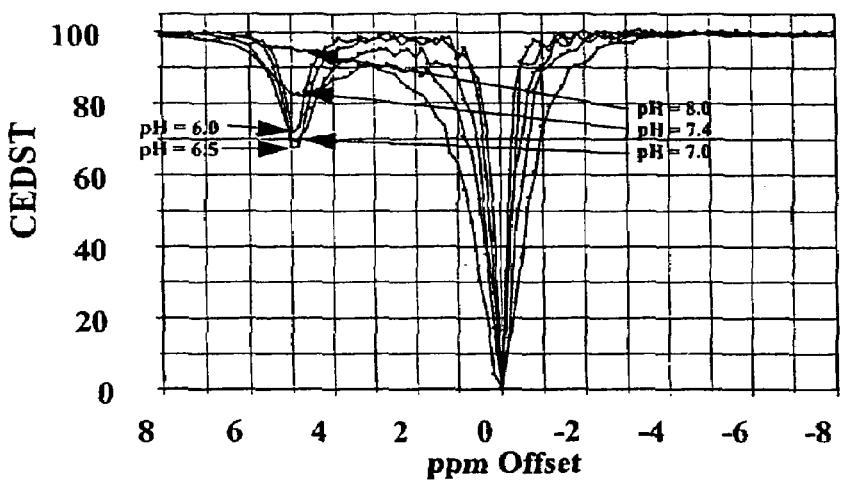
FIG. 2 is a CEDST spectra for 62.5 mM barbituric acid at 37° C. and varying pH values.
Figure 3:
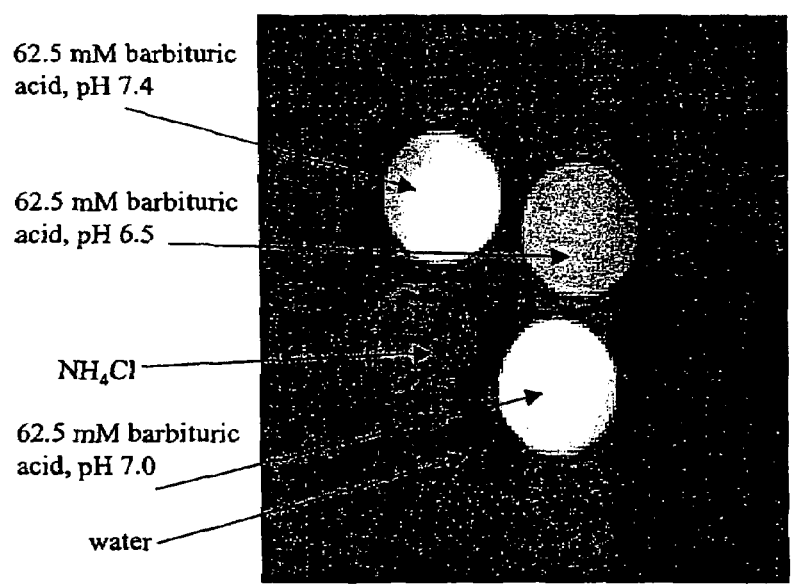
FIG. 3 is a digital MR image of a 62.5 mM barbituric acid solution at different pH values and $NH_4Cl$ as a control, 37° C., illustrating the image enhancement obtained using barbituric acid as a contrast agent.

The CEDST spectra of barbituric acid (62.5 mM, 37° C.) as a function of pH are presented in FIG. 2, while an imaging series of barbiturate-containing phantoms is presented in FIG. 3. As shown in FIG. 2, at 37° C. the exchange optimum for barbituric acid is approximately pH 6.5. FIG. 2 also demonstrates that increasing the pH of the barbituric acid caused the rate of proton exchange to approach fast exchange (where $\Delta\omega_{CA}/K_{CA}$ is less than 1, or where $\Delta\omega_{CA} \ll K_{CA}$).

The results in FIG. 3 confirm those of FIG. 2. MR images of phantoms were collected on a custom-designed 4T system operating at room temperature (about 20° C.). The imaging sequence itself is a GRE (Gradient Recalled Echo) imaging sequence with an off-resonance saturation pulse centered at an offset of 5.00 ppm (850 Hz for the field at 4 Tesla). The other parameters used were: 90 degree flip angle used, TE (Echo time)=9 msec, TR (Repetition time)=1.2 sec, 16 Sinc pulses, followed by crusher gradients (which completely dephased the transverse magnetization). Four test tubes are shown in FIG. 3, with each containing a different solution. Three contained 62.5 mM barbituric acid at pH=7.4, 7.0, or 6.5. The fourth test tube contained 500 mM $NH_4Cl$ at pH=5.0. These test tubes were placed inside the 4T NMR imaging system, irradiated at ±850 Hz, and both control and experimental images were collected as described previously. FIG. 3 is the difference image generated by subtracting the experimental image from the control image. All three solutions of barbituric acid were enhanced, while neither the surrounding water nor the $NH_4Cl$ control were significantly affected. Therefore, the signals in these phantoms were generated due to proton chemical exchange with barbituric acid. The brightest signal in these phantoms (where the control and experimental image difference was the greatest) was generated by barbituric acid at pH=7.4.

Figure 4:
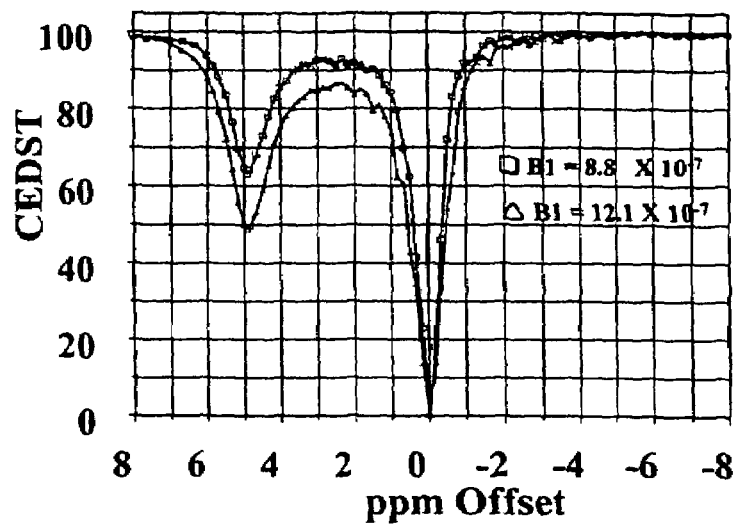
FIG. 4 is a CEDST spectra of an aqueous 125 mM barbituric acid solution (pH=7.0, 37° C.) at two different saturation power levels, 8.8 and $12.1 \times 10^{-7}$T.
Figure 5:
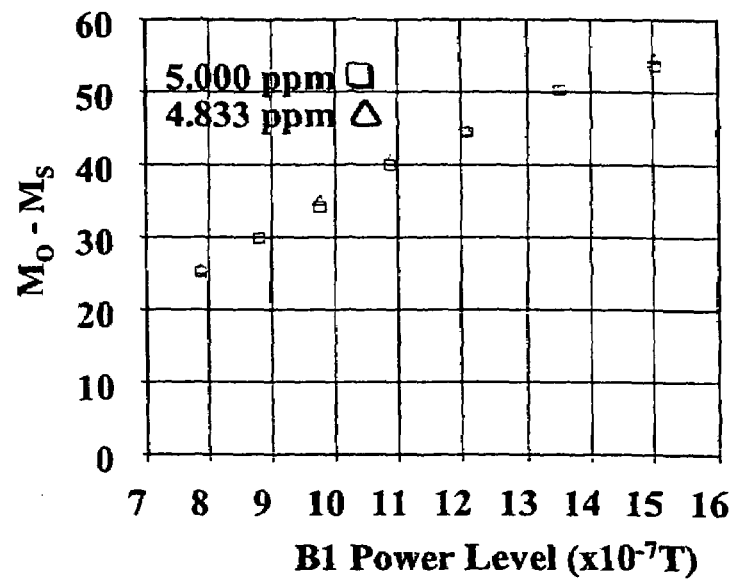
FIG. 5 is a graph of B1 power level$\times 10^{-7}$ T versus $M_O-M_S$ for the exchangeable protons resonating at 4.833 ppm and 5.000 ppm of an aqueous 125 mM barbituric acid solution (pH=7.0, 37° C.).
Figure 19:
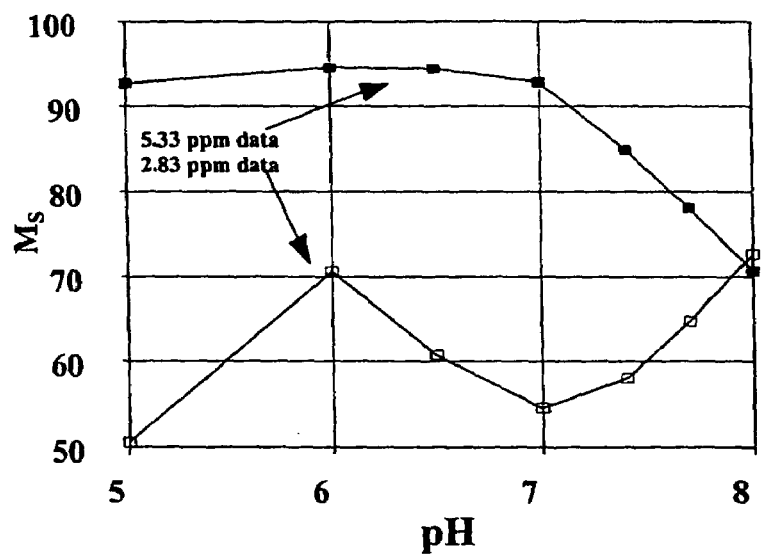
FIG. 19 is $M_S$ data versus pH for the exchangeable protons of 5-hydroxytryptophan and 2-Imidazolidinethione.
Figure 20:
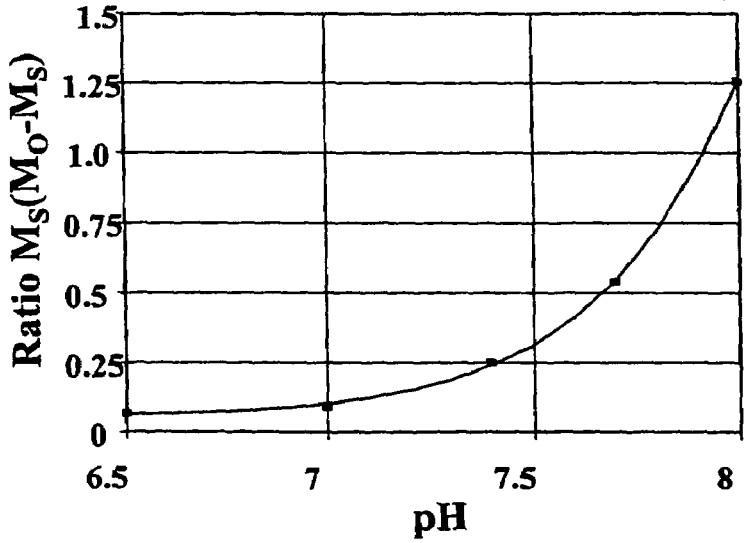
FIG. 20 is data ±SE from 3 experimental runs at each pH and sigmoidal curve fit of ratio $M_S$ $(M_O-M_S)$ versus pH for the combination solution (62.5 mM 5-hydroxytryptophan and 2-Imidazolidinethione, 5.33 ppm: Site 1; 2.83 ppm: Site 2) where ratio $M_S(M_O-M_S)$ is defined as $M_S^{Site\ 2}(M_O-M_S)^{Site\ 1}/[M_S^{Site\ 1}(M_O-M_S)^{Site\ 2}]$.
Figure 25:
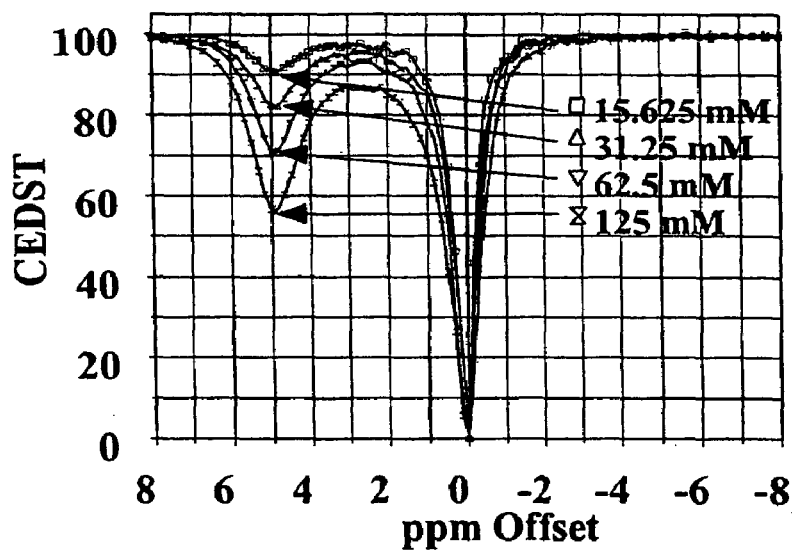
FIG. 25 is a CEDST spectra illustrating the concentration dependence of barbituric acid at pH=7.0, temperature=37° C.
Figure 26:
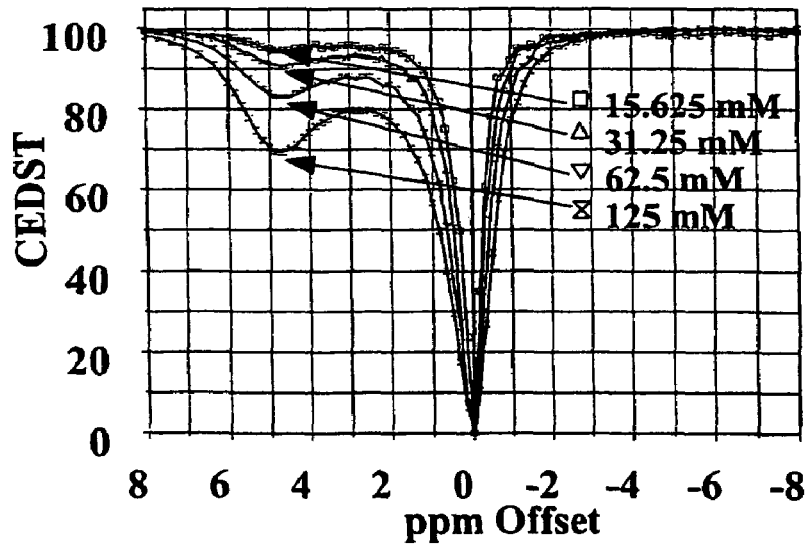
FIG. 26 is a CEDST spectra illustrating the concentration dependence of barbituric acid at pH=7.4, temperature=37° C.

Concentration-dependent effects for barbituric acid were demonstrated (FIGS. 25-26). As shown in these figures, increases in agent concentration increase the available contrast by increasing ($M_O-M_S$). Temperature (FIGS. 18-20) and saturation power effects (FIGS. 4-5) were also characterized. As shown in FIG. 4, increasing the power level from $8.8 \times 10^{-7}$ T to $12 \times 10^{-7}$ T increases the contrast by increasing ($M_O-M_S$). As shown in FIG. 5, increasing the saturation power level increases the ST effect with an optimization at about $16 \times 10^{-7}$ T.

Figure 6:
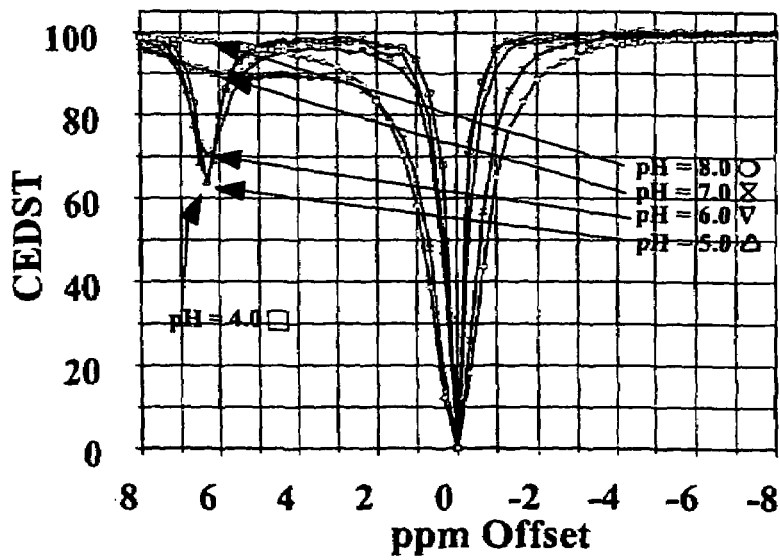
FIG. 6 is a CEDST spectra of 62.5 mM 2-thio-barbituric acid in 20 mM phosphate buffer, 37° C., at pH values 4, 5, 6, 7 and 8.
Figure 7:
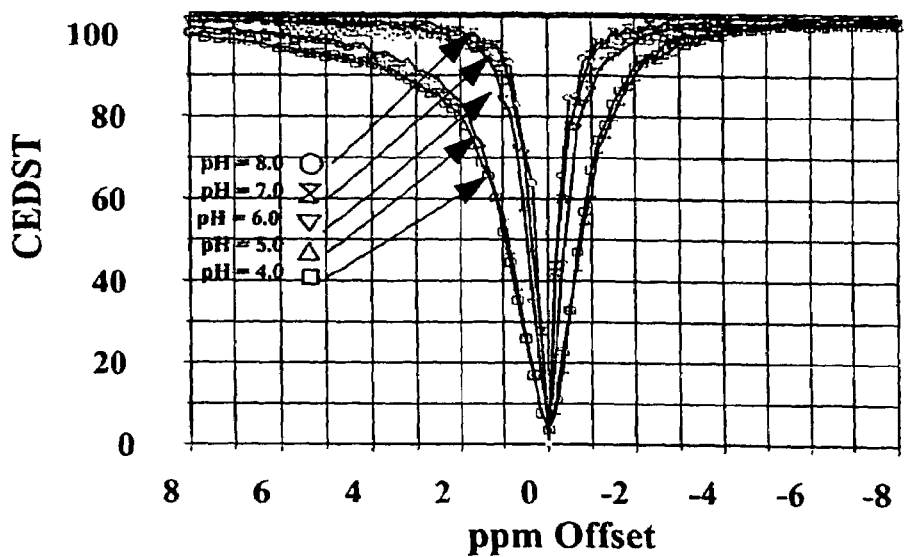
FIG. 7 is a CEDST spectra of 62.5 mM 5,5-diethyl-barbituric acid, in 20 mM phosphate buffer, 37° C., at pH values 4, 5, 6, 7, and 8.

Two derivatives of barbituric acid, 2-thio-barbituric acid (FIG. 6) (barbituric acid with a sulfur substitution for the oxygen at C-2) and 5,5-diethyl-barbituric acid (FIG. 7) (barbituric acid with two ethyl groups substituted for the hydrogens at C-5) also were examined at varying pH levels. As shown in FIG. 6, the substitution of sulfur for oxygen at C-2 results in a peak shift from 5.00 ppm to 6.33 ppm, and a shift of the pH value at the peak ST effect, from pH=6.5 to pH=4.0. This substitution improved the ppm offset value, but the change in pKa resulted in near fast exchange rates at physiological pH. Therefore, this compound is not as useful for use as a contrast agent for saturation transfer at physiological pH. As shown in FIG. 7, the 5.00 ppm site is completely lost due to the loss of both hydrogens at C-5 in barbituric acid (compare to FIG. 2), and the pKa at the exchange site decreases from pH 12 to pH 7.

Barbituric acid is the parent chemical of all barbiturates, but is not itself pharmacologically active. Oral dosage toxicity is quite low, $LD_{50}$>5 g/kg. Goldenthal, *Toxicol. Appl. Pharmacol.*, 18:185, 1971. Substitutions at groups of barbituric acid not involved in chemical exchange are used to manufacture a wide variety of derivative drugs. This same site can be used to polymerize the compound, which would reduce the osmotic stress associated with mmoles of exchange sites of monomers.

Figure 8:
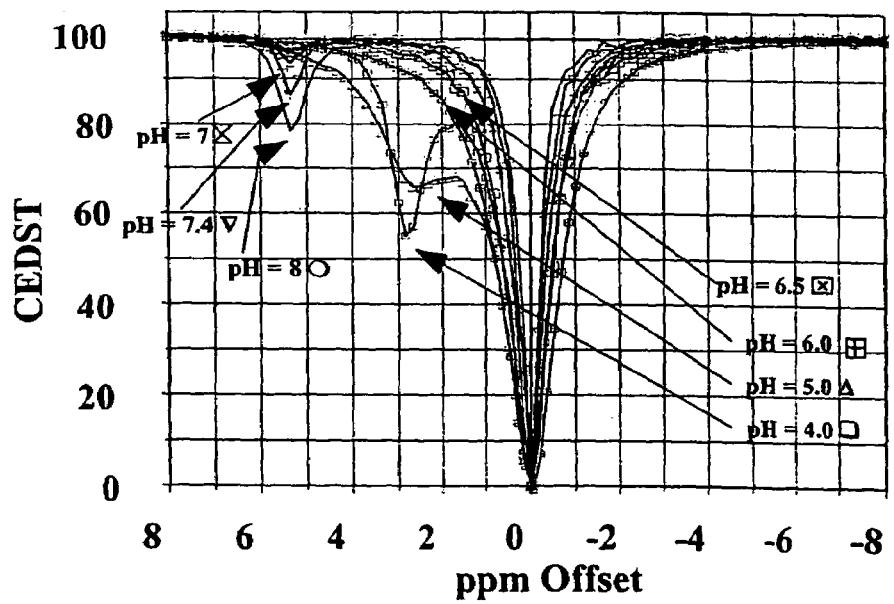
FIG. 8 is a CEDST spectra of aqueous 5-hydroxy-tryptophan solutions 62.5 mM, 37° C., 20 mM phosphate buffer at varying pH levels.

The amino acid analog 5-hydroxy-tryptophan also was characterized for its proton chemical exchange with water. As shown in FIG. 8, 5-hydroxy-tryptophan solutions combine an exchange site at 5.33 ppm with decreasing $M_S$ levels as the pH increased from pH 7.0 to pH 8.0, across the range of physiologic pH. Therefore, 5-hydroxy-tryptophan maintains the desired slow proton chemical exchange at both a desirable pH range and ppm offset, making it a chemical useful in a working embodiment of the present invention due to its combination of characteristics.

EXAMPLE 2

This example describes the in vivo analysis of barbituric acid in a rabbit bladder. A male New Zealand White rabbit (1.5 kg, Hazelton Research Products, Denver Pa.) was initially anaesthetized with an intramuscular injection of a mixture of ketamine/acepromazine (180 mg/2 mg), intubated and placed on a Siemens 900c ventilator (Siemens Medical Systems, Danvers Mass.). A catheter was placed in the marginal ear vein for infusion of intravenous fluids to maintain volume status. This catheter also was used to administer three doses of 50 mL barbituric acid solution (125 mM, pH=7.4, 20 mM phosphate buffer). Anesthesia was maintained with 2% isoflurane until sacrifice with 6 meq of KCl IV.

The barbituric acid reached the kidneys within 20 minutes and was then immediately filtered into the bladder. The rabbit appeared to be physiologically unaltered (i.e. no change in blood pressure) in response to the barbituric acid injection.

Figure 9:
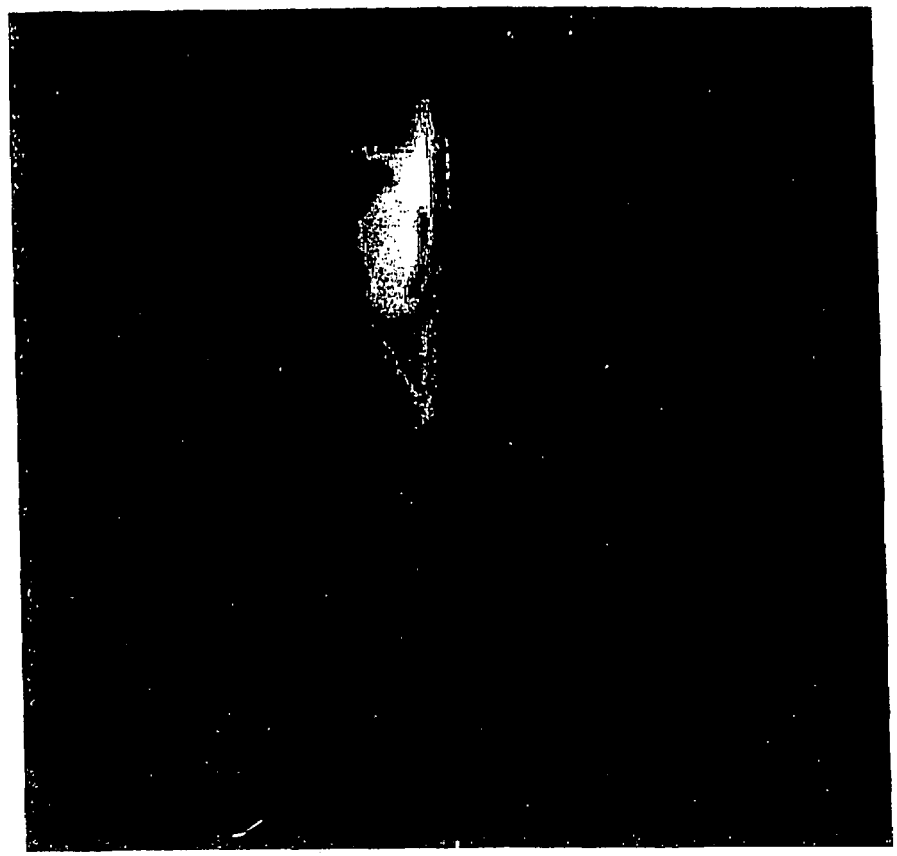
FIG. 9 is a digital control in vivo image of a rabbit bladder obtained following a saturating irradiation centered at −900 Hz (5.25 ppm/4T) off the water resonance peak following administration of barbituric acid (125 mM/pH=7.4/20 mM phosphate buffer).
Figure 10:
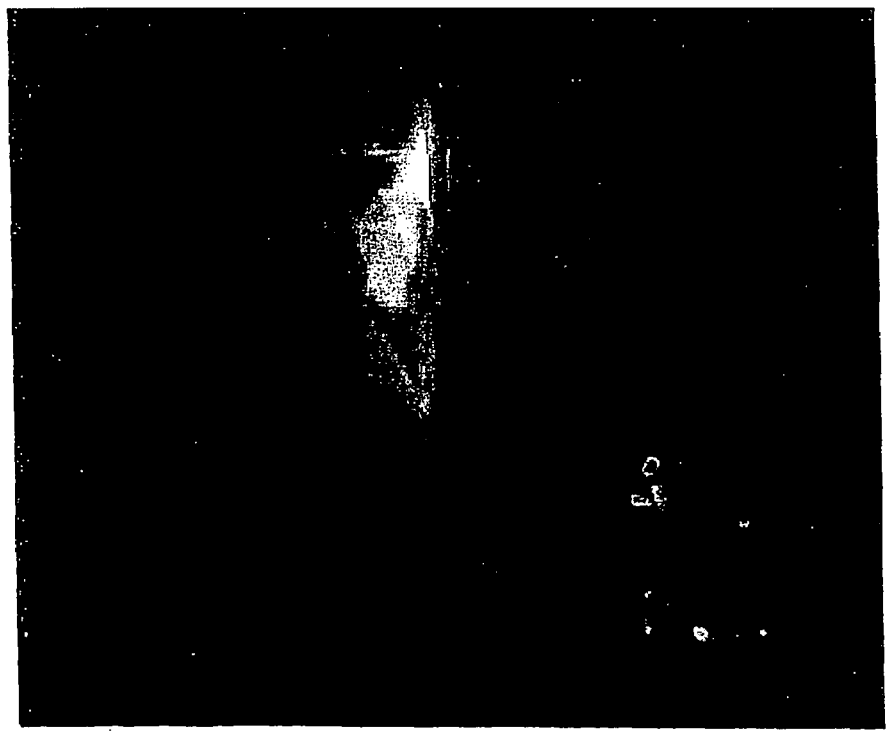
FIG. 10 is a digital in vivo image of a rabbit bladder obtained following a saturating irradiation centered at +900 Hz (5.25 ppm/4T) off the water resonance peak following administration of barbituric acid (125 mM/pH=7.4/20 mM phosphate buffer).
Figure 11:
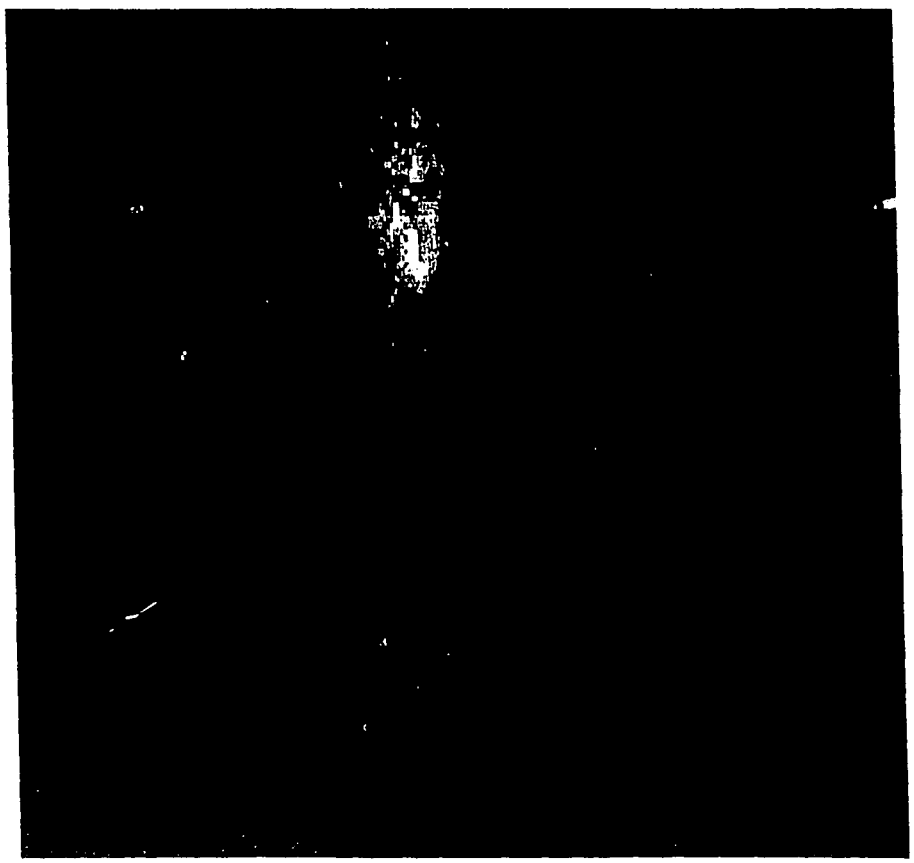
FIG. 11 is a digital difference image (i.e., FIG. 9 image-FIG. 10 image) illustrating the location of the metabolite irradiated at +900 Hz (5.25 ppm/4T) in the in vivo rabbit bladder following administration of barbituric acid (125 mM/pH=7.4/20 mM phosphate buffer).

The rabbit was analyzed using a 4 Tesla magnet at the settings described in Example 1. The images were obtained after irradiation at the ppm offset characteristic of barbituric acid (5.25). FIG. 9 shows the control image following saturating irradiation at −900 Hz (−5.25 ppm/4T) off the water resonance peak. The bladder and surrounding muscles are visible. This control image is collected to correct for the broad background of saturation transfer from macromolecules (i.e. proteins, lipids) located underneath the water signal. Guivel-Scharen et al., *J. Magn. Reson.*, 133:36-45 (1998), herein incorporated by reference. FIG. 10 shows the image of the in vivo rabbit bladder following saturating irradiation centered at +900 Hz (5.25 ppm/4T) off the water resonance peak. This will irradiate the barbituric acid signal. As shown in FIG. 10, the signal decreases in the bladder subsequent to irradiation at 5.25 ppm. FIG. 11 shows the results of subtracting the in vivo image (FIG. 10) from the control image (FIG. 9). As shown in FIG. 11, the only signal remaining after subtracting the non-specific signal (FIG. 9), is in the bladder, not in the muscle or other tissues. These results demonstrate that saturation transfer can be used to enhance the contrast produced in an MR image of a tissue region containing an exogenously administered contrast agent, such as barbituric acid.

Figure 12:
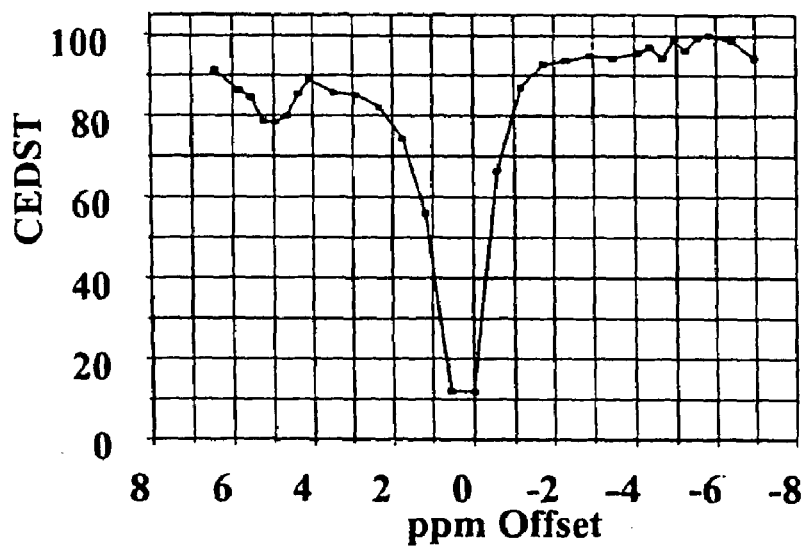
FIG. 12 is a CEDST spectra showing of the in vivo rabbit bladder described in FIGS. 8-10.
Figure 13:
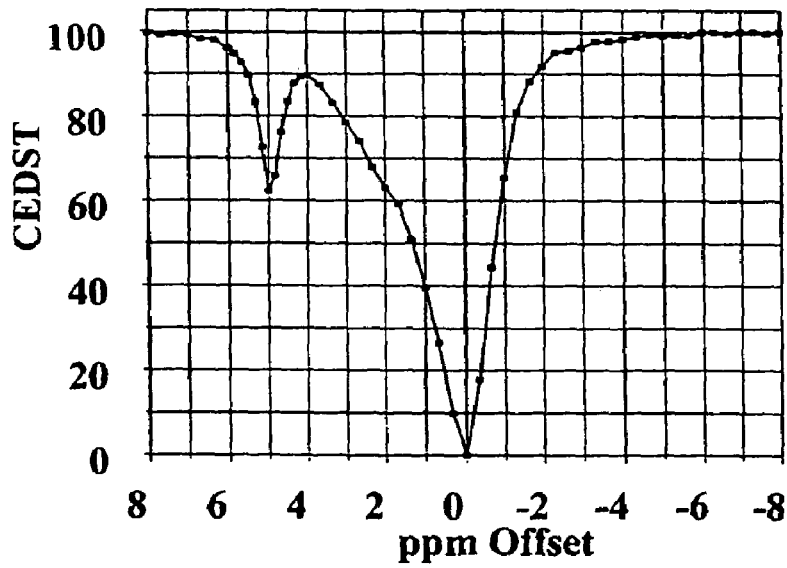
FIG. 13 is an ex vivo rabbit urine CEDST spectra, at 37° C. and a pH of 5.2.
Figure 14:
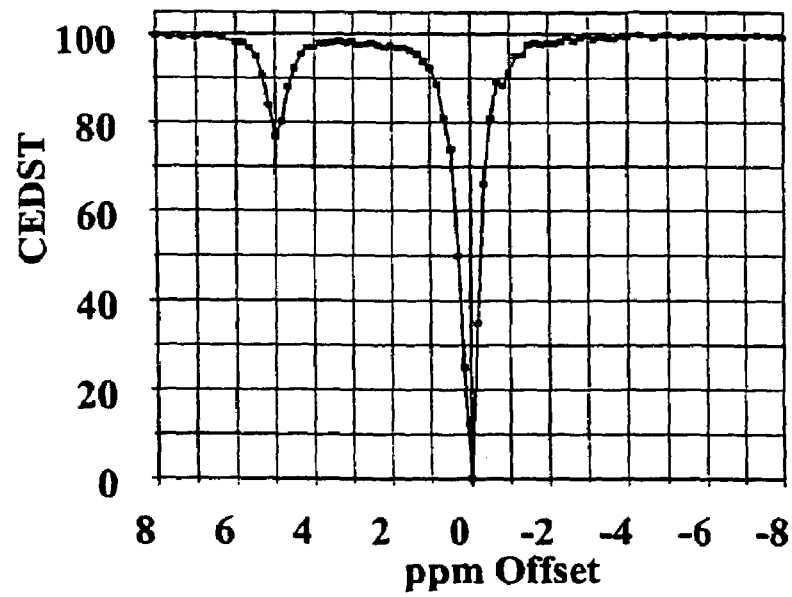
FIG. 14 is a CEDST spectra of a buffered barbituric acid solution (62.5 mM, pH 5.0, 37° C., 20 mM phosphate buffer).

Following sacrifice of the rabbit, urine was collected and evaluated on the 7T system at 37° C. as described in Example 1. FIG. 12 shows the in vivo CEDST spectrum of the bladder, obtained from the brightest section of FIG. 11. The peak at 5.25 ppm (900 Hz) off the water resonance (located at 0 ppm) demonstrates the specificity of the in vivo effect at 5.25 ppm. FIG. 13 shows the ex vivo CEDST spectrum of the urine collected from the sacrificed rabbit (pH 5.2, 37° C.). FIG. 14 shows the CEDST spectrum of a pure barbituric acid solution (62.5 mM, 20 mM phosphate buffer, pH 5.0, 37° C.). The spectrum shown in FIGS. 12-14 demonstrate the validity of the specific location of the ppm offset used in the in vivo imaging sequence (FIGS. 9-11). FIGS. 12-14 also confirm the identity of the metabolite imaged during the in vivo analysis.

EXAMPLE 3

This example teaches how to determine pH using water proton NMR in combination with one or more exogenously added compounds. Magnetic resonance spectroscopy can provide pH measurements using the chemical shift differences between chemical moieties in vivo. Pan et al., *Proc. Nail. Acad. Sci. USA.*, 85:7836; 1988; Mitsumori, *J. Biochem.*, 97:1551;1985; Petersen et al., *Magn. Reson. Med.*, 4:341;1987. However, most of these metabolites are in low concentration, making high resolution imaging or rapid determinations of pH difficult. Therefore, a method was developed to obtain pH information from the intensity of the water proton resonance to improve the signal-to-noise of pH measurements by detecting pH-sensitive, water-proton chemical exchange with selected molecules using CEDST.

The pH affects the net chemical exchange reaction rate ($K_{CA}$) by varying the concentration of the $H^+$ and/or $OH^-$ reactants. Thus, through its effect on $K_{CA}$, changes in pH will affect saturation transfer signals from water as indicated in Equation 1.

$$M_S/M_O \sim 1/(1+k_{CA}T_{1W}) \quad \text{Equation 1}$$

As stated above, $M_S$ is the magnitude of the water proton signal in the presence of contrast agent proton saturation; $M_o$ is the magnitude of the signal under control irradiation at the opposite frequency offset; $K_{CA}$ is the site proton exchange rate constant; and $T_{1W}$ is the spin lattice relaxation rate of water protons. To use CEDST to determine $K_{CA}$, the exchange site should have an adequate $\Delta\omega_{CA}$ and be in the slow-to-intermediate exchange domain (Equation 3), where $\Delta\omega_{CA} > K_{CA}$. After calibrating the effects of pH on $K_{CA}$, $M_S/M_O$ can be used to determine pH.

To resolve the exchange site chemical shift, $\Delta\omega_{CA}/k_{CA}$ should be greater than 1, where $\Delta\omega_{CA}$ is the chemical shift between water protons and the exchange site. A large $\Delta\omega_{CA}$ permits a high exchange rate while remaining in the slow-to-intermediate exchange domain. A high exchange rate decreases the $M_S/M_O$ ratio (see Equation 1) improving the CEST effect and subsequent signal to noise for the pH determination. A large $\Delta\omega_{CA}$ also minimizes problems associated with magnetic field susceptibilities and background macromolecular interference. Ward et al. *J. Magn. Res.*, 143:79 (2000). The concentration of the exchange sites must be on the order of 40 mM to generate a significant $M_S/M_O$ effects the limitations in proton $\Delta\omega_{CA}$. The chemical shift of protons in most biomolecules is quite small, but can be greatly enhanced with associated metals (for example: Fe in myoglobin, Jue and Anderson. *Magn. Reson. Med.* 13:524 (1990)). The use of the chemical shift enhancing approaches may extend the application of this method.

A method to eliminate obtaining additional measurements and background effects is to use a single molecule agent with two or more exchange sites with different chemical shifts and pH dependencies. The relationship for each of the two sites on a dual-exchange site CEDST agent (Site 1 and Site 2) can be represented as follows:

$$(M_O-M_S)^{Site\ 1}/M_S^{Site\ 1}=k_{CA}^{Site\ 1}[\text{Agent}]^{Site\ 1}n^{Site\ 1}T_{1W} \quad \text{Equation 4}$$

$$(M_O-M_S)^{Site\ 2}/M_S^{Site\ 2}=k_{CA}^{Site\ 2}[\text{Agent}]^{Site\ 2}n^{Site\ 2}T_{1W} \quad \text{Equation 5}$$

The ratio of these two equations reduces to:

$$M_S^{Site\ 2}(M_O-M_S)^{Site\ 1}/[M_S^{Site\ 1}(M_O-M_S)^{Site\ 2}]=k_{CA}^{Site\ 1}[\text{Agent}]^{Site\ 1}n^{Site\ 1}/k_{CA}^{Site\ 2}[\text{Agent}]^{Site\ 2}n^{Site\ 2} \quad \text{Equation 6}$$

As seen in Equation 6, the ratio of $M_S^{Site\ 2}(M_O-M_S)^{Site\ 1}/[M_S^{Site\ 1}(M_O-M_S)^{Site}]$ is equivalent to the ratio of the site $k_1$ values ($k_1^{Site}=k_{CA}^{Site}[\text{Agent}]^{Site}n^{Site}$) that vary with pH. For a molecule with both Site 1 and Site 2, the [Agent] and [n] terms cancel to leave a ratio of the site $K_{CA}$ values. If Site 1 and Site 2 are on different molecules, the ratio of (Agent) [n] is required. Based on the relationship illustrated in Equation 6 the $M_S^{Site\ 2}(M_O-M_S)^{Site\ 1}/[M_S^{Site\ 1}(M_O-M_S)^{Site\ 2}]$ data for two different sites plotted as a function of pH can be used to create a standard curve that eliminates effects associated with $T_{1W}$, [Agent] and [n]. Based on these theoretical advantages of multiple exchange sites with different pH dependencies, this approach was utilized.

Test compounds were dissolved in HPLC water and pH-specific inorganic phosphate buffers as described in Example 1 to maintain pH. Phosphate buffer concentration affected CEDST results (see Example 1) and was held constant at 20 mM. Several chemical reagents, including 5,6-dihydrouracil, 5-hydroxy-tryptophan, hydantoin, parabanic acid, sugars, amino acids, nucleosides, and imidazoles (Table 1), were tested for their ability to undergo proton chemical exchange detected using CEDST. Chemical shifts are reported relative to the water resonance. The spectral dependence of CEDST was determined by sweeping the irradiation frequency and while monitoring the water resonance. CEDST spectra were acquired at 7T using a Bruker AC-300 wide bore spectrometer at 37° C.±0.1° C. The observation frequency was set on the water peak and the decoupler was used to provide off-resonance saturation. Studies were conducted using a steady-state with irradiation (15 seconds) over a range of irradiation frequencies±8.00 ppm from water. CEDST spectra were plotted in the form of water amplitude ($M_S$) versus irradiation frequency.

Saturation depends on the B1 power and the irradiation offset frequency. The appropriate power was determined by increasing power until no further decrease in $M_S$ was observed. In most samples this occurred with a B1~14.7× $10^{-7}$T. Due to the differences in T2 associated with the exchange rate, power requirements were calibrated for each experiment. Pulse sequence parameters: PW=8.0 μsec (1.47×$10^{-6}$T; Flip angle=90°), one acquisition/Hz offset, 8192 data points, resolution of 0.97 Hz/pt, SW=8000 Hz. Spin lattice relaxation time constants (T1) were obtained with inversion-recovery experiments. The range of inversion delays (Ti) was between 0.001 and 30 seconds, with a 30 second pre-delay.

Figure 15:
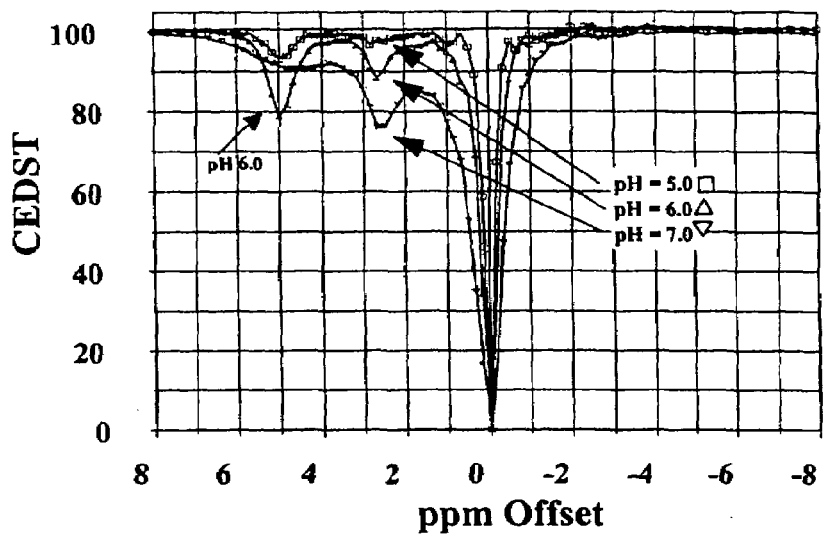
FIG. 15 provides the CEDST spectrum of 62.5 mM 5,6-dihydrouracil, T=37° C., at pH values of 5.0, 6.0 and 7.0.

The ratiometric analyses required separate $M_S$ and $M_O$ determinations for two sites. Three complete CEST spectra were analyzed to calculate the average and SEM of each of these parameters per experimental solution. Plots of the ratios versus pH were then analyzed with Sigma Plot to provide the Hill plot curve fit parameters and R2 values Initial studies identified several molecules with desirable chemical exchange and shift characteristics. With a single site, the $T_{1W}$ is determined, which reduces the speed and accuracy of the measurement. To overcome this limitation, agents with two or more exchange sites with different chemical shifts and pH dependencies can be used. In this example, agents with two different exchange sites were used in a ratiometric fashion to determine the pH independent of $T_{1W}$. A representative molecule, 5,6-dihydrouracil, has two exchange sites, one at 5.0 and the other at 2.67 ppm, each with a different pKa (FIG. 15). The exchange site at 5.0 ppm optimizes at pH 6, while the exchange site at 2.67 optimizes at pH 7. At pH 5.0, the 2.67 ppm site is slow, while the 5.00 ppm site is faster resulting in a CEDST effect. At pH 6.0, the 2.67 ppm site is now fast enough to be observed while the effect at 5.00 ppm has increased further. At pH 7.0, the 2.67 ppm site has increased while the 5.00 ppm peak has entered an intermediate exchange rate resulting in a chemical shift towards the water pool resonance and a broadening of the CEDST spectrum.

Figure 16:
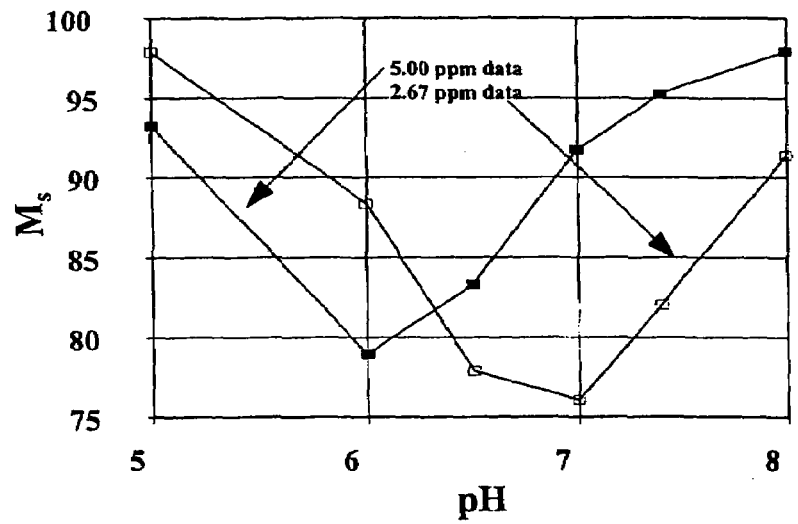
FIG. 16 is $M_S$ data versus pH for both exchangeable protons of 5,6-dihydrouracil.
Figure 17:
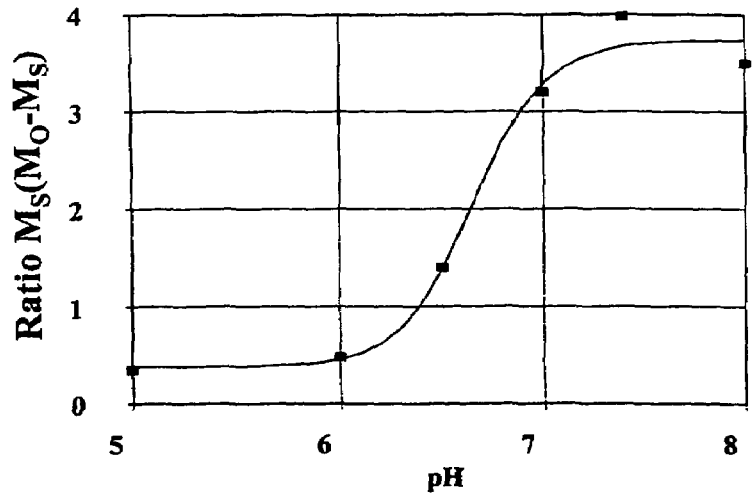
FIG. 17 is data ±SE from 3 experimental runs at each pH and curve fit of ratio $(M_O-M_S)$, defined as $(M_O-M_S)^{Site\ 1}/(M_O-M_S)^{Site\ 2}$ versus pH for 5,6-Dihydrouracil (2.67 ppm: Site 1; 5.00 ppm: Site 2).

Plotting the individual $M_S$ values as a function of pH (FIG. 16) shows that each exchange site reaches a minimum $M_S$ value as the intermediate exchange condition is reached. Above this point, the $M_S$ value increases again due to exchange broadening and frequency shift effects. A hyperbolic standard curve (FIG. 17) is produced by plotting the ratio $M_S^{Site\ 2}(M_O-M_S)^{Site\ 1}/[M_S^{Site\ 1}(M_O-M_S)^{Site\ 2}]$ (±SE from 3 experiments; Site 1: 2.67 ppm, Site 2: 5.00 ppm) as a function of pH. These results show that 5,6-dihydrouracil is effective in the pH region of 6.5. However another agent with two exchange sties at 5.33 and 2.83 ppm, 5-hydroxytryptophan (5-HT), (see FIG. 8 and Example 1) is a good contrast agent at physiologic pH. The pH dependence of the minimum $M_S$ values occurred at pH 4 and 8 respectively, but did not significantly overlap in intermediate pH values. This resulted in a poor ratiometric performance.

Since both exchange sites on 5,6-dihyrouracil have the same dependence on $T_{1W}$ and the approach to fast exchange is independent of T1, the relationship between pH and ratio of $(M_O-M_S)$ is independent of $T_{1W}$. The standard calibration curve is field dependent, however, due to the field-specific effect on $\Delta\omega_{CA}$.

$$\Delta\omega_{CA}=(ppm)*(Field)(2\pi) \qquad \text{Equation 7}$$

With reference to Equation 7, ppm is chemical shift difference of contrast agent in part-per-million units; and (Field) is the proton resonance frequency in MHz of the specific magnetic field (i.e., a 7T field operates at 300 MHz, a 4T field operates at 171 Mhz, and a 1.5T field operates at 63.6 MHz). The shift in $\Delta\omega_{CA}$ when at a lower magnetic field will change the slow-to-intermediate exchange limit (Equation 3) since the condition $\Delta\omega_{CA}>K_{CA}$, must still be satisfied. The standard calibration curve is field dependent due to the fast exchange dependence on frequency difference.

Figure 18:
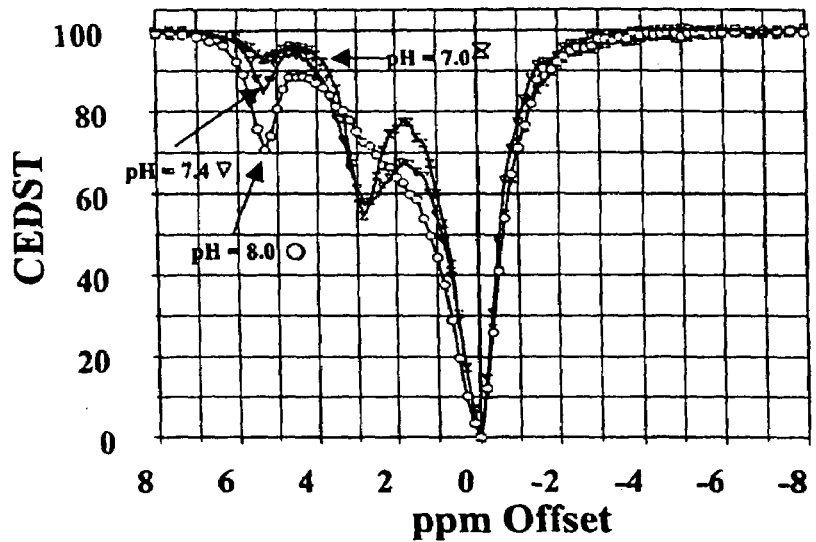
FIG. 18 provides the CEDST spectrum of a solution containing 62.5 mM 5-hydroxytryptophan and 2-Imidazolidinethione at pH 7.0, 7.4, and 8.0.

Exchange sites on two different molecules can also be used to measure pH. This permits a larger number of sites to be evaluated as well as a method of fine-tuning the pH sensitivity. These experiments were conducted on solutions containing two separate chemical exchange agents. CEDST spectra from a solution containing 62.5 mM 5-Hydroxytryptophan (5-HT) and 2-Imidazolidinethione (2-IL) at different pH values is shown in FIG. 18. Plotting the individual $M_S$ values as a function of pH (FIG. 19) shows that the 2-IL 2.83 ppm exchange site reaches minimum $M_S$ at pH 7.0, while the 5-HT site at 5.33 ppm remains in slow exchange up to pH 8.0. The ratiometric analysis was performed on these two sites at 5.33 and 2.83 ppm. Good sensitivity over the physiological pH range was observed (see FIG. 20).

Figure 21:
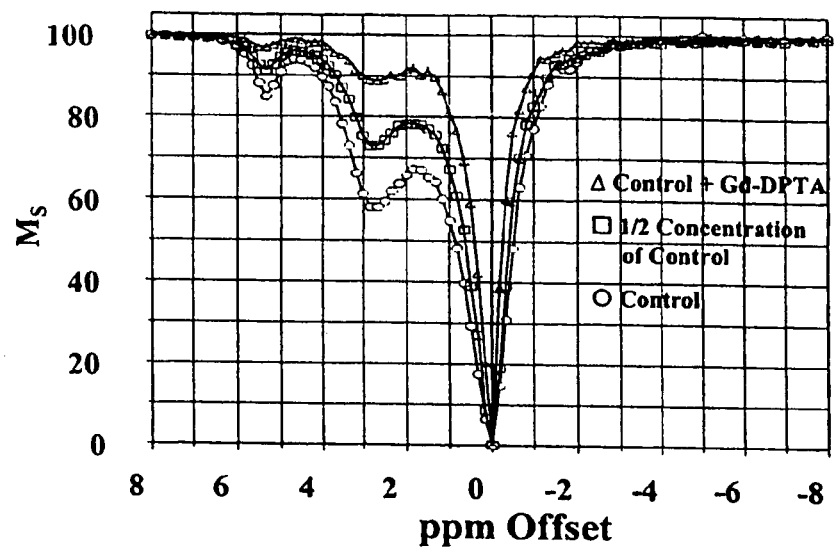
FIG. 21 is a CEDST spectra for: control solution containing 5-HT and 2-IL, half the concentration of the control solution, and the control solution plus Gd-DPTA measured at pH=7.4, showing the effect of agent concentration and water T1 on CEDST effects.

The ability of the ratiometric technique to determine pH independent of the concentration of the contrast agent ([Agent]) or $T_{1W}$ was evaluated by altering [Agent] or adding Gd-DPTA (gadolinium diethylenetriaminepentaacetic acid). CEDST data from three solutions (all at pH 7.4) is presented in FIG. 21: Control (62.5 mM each 5-HT and 2-IL) (solution 1); ½ Concentration of Control (31.25 mM each 5-HT and 2-IL) (solution 2); and Control+Gd-DPTA (62.5 mM each 5-HT and 2-IL plus 1 µl Gd-DPTA/ml) (solution 3). The T1 of the control solution (4.05+0.07 sec, n=7), and solution 2 (T1=3.96+0.08 sec, n=7), were the same at ~4 sec, while solution 3 was reduced to 0.56+0.03 sec (n=7). CEDST data were collected as a function of pH (pH 5.0, 6.0, 6.5, 7.0, 7.4, 7.7, and 8.0) to perform the ratiometric analysis (Equation 6). As predicted (Equation 1), decreases in either T1 or [Agent] increased $M_S$. However, the pH dependence of the ratio was unchanged at a given pH for each solution using a paired t-test (solution 1 versus solution 2, p=0.22, d.o.f. =6; solution 1 versus solution 3, p=0.08, d.o.f.=6; solution 2 versus solution 3, p=0.63, d.o.f.=6).

The high concentration of exchange sites may provide additional proton buffer capacity for the plasma or cytosol which could affect the pH measurement. However, the optimal pH for $K_{CA}$ and $M_S/M_O$ effects does not necessarily correspond to the pKa of the molecule where the buffering capacity is maximized. For example, the pKa of the 5.00 ppm site on 5,6-dihydrouracil is ~9.5 while pH 6.0 is the optimal pH for $M_S$ effects, well away from its buffer capacity maximum. This occurs because when the concentration of the base increases above a few percent, the exchange rate moves into the fast exchange limit in this molecule. Thus, the proton buffering capacity of these probes may not be a problem for pH measurements.

This example demonstrates that detection of the chemical exchange rate, $K_{CA}$, using CEDST techniques, can determine pH using the amplitude of the water signal and $T_{1W}$. The use of the water proton signal in detecting pH resulted in a several hundred-fold enhancement of signal-to-noise over the direct chemical shift detection schemes. This may permit rapid kinetic studies or the eventual imaging of the distribution of pH in biological samples. The multiple molecule approach allows the optimization of the chemical exchange sites for a given pH range and may serve as a useful model system to guide the synthesis of appropriate single molecule probes for in vitro and in vivo studies.

This method can be used to determine pH in vivo using external contrast agents and CEDST. The method would involve selecting one or more appropriate contrast agents and preparing standard pH curves for the one or more contrast agents as described above. The one or more contrast agents would be administered to a subject and CEDST MRI analysis performed by irradiating the subject at the frequencies determined in vitro for the contrast agent. The ratio $M_S^{Site\ 2}(M_O-M_S)^{Site\ 1}/[M_S^{Site\ 1}(M_O-M_S)^{Site\ 2}]$ would then be determined and compared to the standard curve to determine the pH.

In vivo pH measurements are important diagnostic tools. For example, the method can be used to determine the acidosis of a tumor. This information can then be used to select pharmaceuticals for tumor therapy, based on whether a tumor is going acidotic. As another example, in vivo pH measurements can be used to determine the pH of the myocardium to determine if it is ischemic (acidic pH). Furthermore, by comparing the pH of the vasculature entering and leaving the kidney, one can determine if the kidney is ischemic. The fact that these effects do not rely on the use of metals makes the ability to place these probes inside cells feasible using cleavable ester groups as used in optical dyes.

EXAMPLE 4

This example describes the effects of temperature on CEDST MRI images. CEDST spectra of barbituric acid were obtained to evaluate the temperature dependence of 62.5 mM solutions of barbituric acid at both 25° C. and 37° C., and at pH values=7.0, 7.4, and 6.5. The ST spectra were taken using the parameters described in Example 1.

Figure 22:
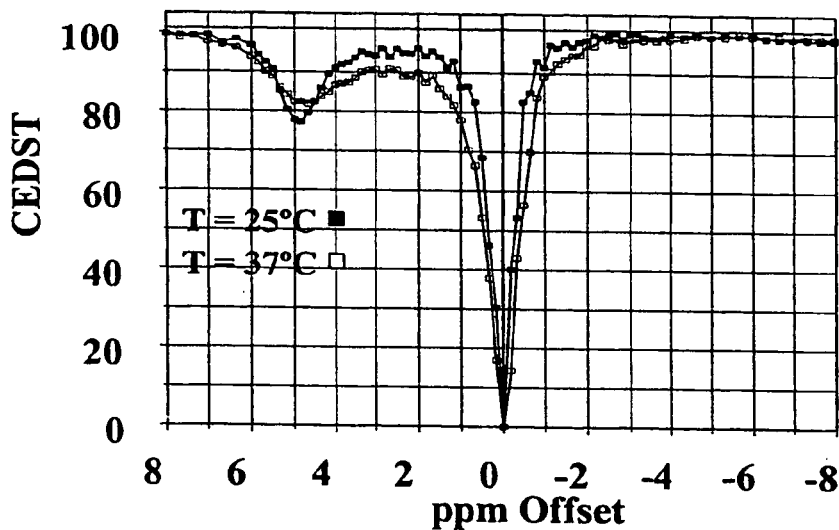
FIG. 22 is a CEDST spectra of 62.5 mM barbituric acid, (pH=7.4, in 20 mM phosphate buffer) measured at 7T at 25° C. and 37° C.
Figure 23:
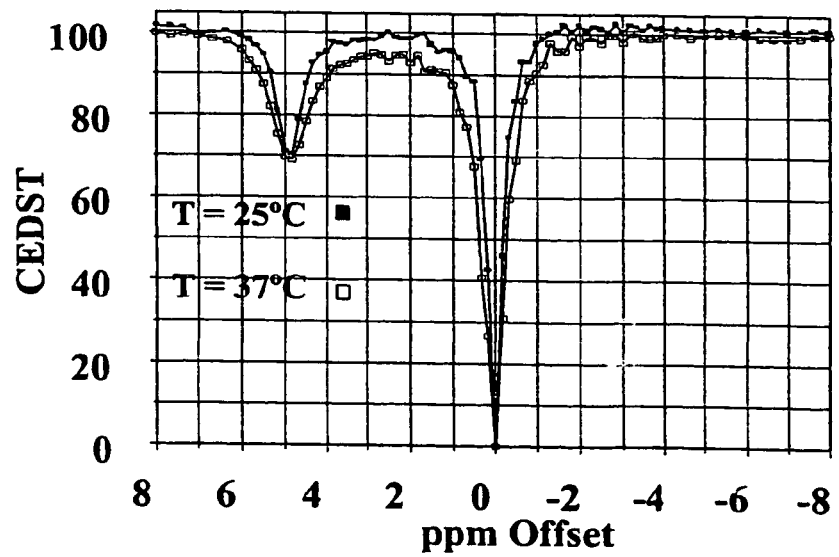
FIG. 23 is a CEDST spectra of 62.5 mM barbituric acid (pH 7.0, 20 mM phosphate buffer) measured at 7T for at 25° C. and 37° C.
Figure 24:
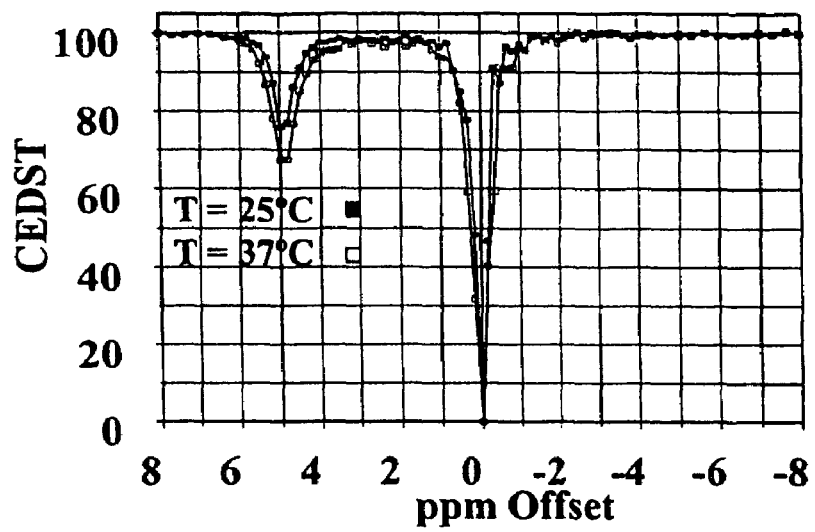
FIG. 24 is a CEDST spectra of 62.5 mM barbituric acid (pH=6.5, 20 mM phosphate buffer) measured at 7T at 25° C. and 37° C.

FIG. 22 is a CEDST spectra illustrating the effects of temperature on a 62.5 mM (pH=7.4, 20 mM phosphate buffer) barbituric acid solution measured at 7T at 25° C. and 37° C. FIG. 23 is a CEDST spectra illustrating the effects of temperature on a 62.5 mM (pH=7.0, 20 mM phosphate buffer) barbituric acid solution measured at 7T at 25° C. and 37° C. FIG. 24 is a CEDST spectra illustrating the effects of temperature comparison on a 62.5 mM (pH=6.5, 20 mM phosphate buffer) barbituric acid solution measured at 7T at 25° C. and 37° C. FIGS. 22-24 show that the CEDST spectra of contrast agents, in this case barbituric acid, can be affected by changes in temperature. In a manner similar to that described in Example 3, temperature dependent standard curves can be produced for a particular contrast agent. Standard temperature dependent curves can be produced through in vitro CEDST analyses of the agent of interest, at fixed pH and phosphate concentrations, as a function of temperature. The shape of a CEDST spectrum changes with changes in temperature (see FIGS. 22-24). This shape can be characterized through a line-shape analysis of the entire CEDST spectrum, or of a subset of the spectrum as a function of temperature to derive the standard temperature calibration curve. A contrast agent possessing two proton chemical exchange sites also can be analyzed as previously described, like the pH and phosphate concentration measurements, by the ratio of $(M_O-M_S)^{Site\ 1}/(M_O-M_S)^{Site\ 2}$ as a function of temperature. Once standard curves are plotted, temperature of a sample, such as the in vivo temperature of tissue, can be determined by first conducting CEDST MRI analyses of the sample using a known contrast agent, and thereafter comparing the results to the standard curve. For example, the method can be used to measure the temperature of tumor as it is being thermally-ablated.

EXAMPLE 5

This example concerns a method for determine metabolite concentrations in vivo, such as a method for determining in vivo phosphate concentration, using external contrast agents and CEDST. As described above in Example 1 and with reference to FIG. 1, the image generated by the contrast agent 5,6-dihydrouracil depends on the phosphate concentration. The ratio of the magnitude of the peaks at 5.00 ppm and 2.67 ppm directly correlates with the phosphate concentration. Thus, phosphate concentration can be determined in vivo by (1) first administering a contrast agent, such as 5,6-dihydrouracil, to the subject, (2) allowing the contrast agent to disperse to the tissue of interest, (3) performing CEDST MRI analysis of the subject by irradiating at ±2.67 ppm and ±5.00 ppm, (4) determining the ratio $(M_O-M_S)^{Site\ 1}/(M_O-M_S)^{Site\ 2}$ (for this example, Site 1:5.00 ppm, Site 2:2.67 ppm), for the subject, and (5) comparing the ratio measured in vivo to known ratios determined in vitro to determine the in vivo phosphate concentration. As the ratio of the peak magnitude increases, so does the phosphate concentration.

Having illustrated and described the principles of obtaining MRI images using one or more contrast agents, it should be apparent to one skilled in the art that the invention can be modified in arrangement and detail without departing from such principles. In view of the many possible embodiments to which the principles of our invention may be applied, it should be recognized that the illustrated embodiments are only examples of the invention and should not be taken as a limitation on the scope of the invention. Rather, the scope of the invention is in accord with the following claims. We therefore claim as our invention all that comes within the scope and spirit of these claims.

We claim:

1. A method for determining the in vivo concentration of a metabolite, comprising:
   administering a contrast agent to a subject;
   allowing the contrast agent to disperse to tissue of interest;
   performing chemical exchange dependent saturation transfer MRI analysis of the subject
   comparing results of the MRI analysis to known in vitro results to determine metabolite concentration.

2. The method according to claim 1 where the contrast agent is 5,6-dihydrouracil.

3. The method according to claim 2 where the metabolite is phosphate.

4. The method according to claim 2 and further comprising irradiating at 2.67 ppm and 5.00 ppm on both sides of a water peak and then determining a ratio of $(M_O-M_S)^{Site\ 1}/(M_O-M_S)^{Site\ 2}$, where site 1 resonates at 5.00 ppm, and site 2 resonates at 2.67 ppm and $M_S$ represents a magnitude of a water proton signal in presence of contrast agent proton saturation and $M_O$ represents a magnitude of a signal under control irradiation at an opposite frequency offset.

5. The method according to claim 1 wherein the contrast agent is administered as an aqueous composition comprising an aqueous mixture of at least one contrast agent in amounts sufficient to perform chemical exchange dependent saturation transfer MRI analysis, the contrast agent being selected from the group consisting of sugars and oligomers and polymers thereof, amino acids and oligomers and polymers thereof, nitrogen-containing heterocycles, nucleosides, imidazole and derivatives thereof, imino acids and analogs thereof, barbituric acid and analogs thereof, guanidine, hydantoin, parabanic acid, biologically active salts of the contrast agents, and mixtures of contrast agents.

6. The method of claim 5 where the composition comprises from about 0.25 mM to 250 mM contrast agent.

7. The method of claim 1, where performing chemical exchange dependent saturation transfer MRI analysis comprises:
   selectively irradiating and saturating an exchangeable proton or protons of the contrast agent with an applied magnetic field;
   applying a selective irradiation with an equal but opposite chemical shift difference between the contrast agent proton exchange site and a water proton resonance frequency $()T_{CA}$), thereby providing a first image set with the irradiation ±chemical shift difference between the contrast agent proton exchange site and the water proton resonance frequency $(\pm)T_{CA}$);
   producing a second image set using the first image set.

8. The method of claim 1 where the contrast agent is 5-hydroxy-tryptophan.

9. The method of claim 1 where the contrast agent comprises a tryptophan.

10. A method for determining in vivo phosphate concentration, comprising:
   administering 5,6-dihydrouracil to a subject;
   allowing the contrast agent to disperse to tissue of interest;
   performing chemical exchange dependent saturation transfer MRI analysis of the subject by irradiating at 2.67 ppm and 5.00 ppm on both sides of a water peak;
   determining a ratio of $(M_O-M_S)^{Site\ 1}/(M_O-M_S)^{Site\ 2}$ where site 1 resonates at 5.00 ppm and site 2 resonates at 2.67 ppm, where $M_S$ represents a magnitude of a water proton signal in presence of contrast agent proton saturation and $M_O$ represents a magnitude of a signal under control irradiation at an opposite frequency offset; and
   comparing the determined ratio to known in vitro ratios to determine phosphate concentration.

* * * * *